(12) United States Patent
Akada et al.

(10) Patent No.: US 9,453,233 B2
(45) Date of Patent: Sep. 27, 2016

(54) METHOD FOR PRODUCING KLUYVEROMYCES MARXIANUS TRANSFORMANT

(75) Inventors: Rinji Akada, Ube (JP); Hisashi Hoshida, Ube (JP); Babiker Mohamed Ahmed Abdel-Banat, Ube (JP); Jun Asakawa, Ube (JP)

(73) Assignee: Yamaguchi University, Yamaguchi (JP)

( * ) Notice: Subject to any disclaimer, the term of this patent is extended or adjusted under 35 U.S.C. 154(b) by 629 days.

(21) Appl. No.: 13/634,891

(22) PCT Filed: Feb. 1, 2011

(86) PCT No.: PCT/JP2011/000550
§ 371 (c)(1),
(2), (4) Date: Nov. 8, 2012

(87) PCT Pub. No.: WO2011/114613
PCT Pub. Date: Sep. 22, 2011

(65) Prior Publication Data
US 2013/0059389 A1    Mar. 7, 2013

(30) Foreign Application Priority Data
Mar. 16, 2010 (JP) .................... 2010-058917

(51) Int. Cl.
C12N 15/74    (2006.01)
C12N 15/81    (2006.01)
C12N 15/64    (2006.01)
C07K 14/37    (2006.01)
C12N 1/19     (2006.01)

(52) U.S. Cl.
CPC .............. *C12N 15/815* (2013.01); *C07K 14/37* (2013.01); *C12N 15/64* (2013.01)

(58) Field of Classification Search
None
See application file for complete search history.

(56) References Cited

FOREIGN PATENT DOCUMENTS

JP    2005-229950    9/2005
WO    2009/116286    9/2009

OTHER PUBLICATIONS

European Search Report (EP 11755806.4) dated Jul. 29, 2013.
Nielson, Michael L., et al. "Transient Marker System for Interative Gene Targeting of a Prototrophic Fungus," (Nov. 2007) Applied and Enviromental Microbiology, pp. 7240-7245.
Kitada, Kunio, et al., "Isolation of a Candida glabrata centromere and its use in construction of plasmid vectors," (1996) Gene, pp. 105-108.
Van Dijk, Ralf, et al., "The methylotrophic yeast *Hansenula polymorpha*: a versatile cell factory," (2000) Enzyme and Microbial Technology 26:793-800.
Abdel-Banat, Babiker M.A., "Random and targeted gene integrations through the control of non-homologous end joining in the yeast *Kluyveromyces marxianus*," Yeast (2010) 27:29-39.
Ball, Maria M., "Construction of Efficient Centromeric, Multicopy and Expression Vectors for the Yeast *Kluyveromyces marxianus* Using Homologous Elements and the Promoter of a Purine-Cytosine-Like Permease," J. Mol. Microbiol. Biotechnol. (1999) 1(2):347-353.
Cohen, Stanley N., et al., "Construction of Biologically Functional Bacterial Plasmids In Vitro," Proc. Nat. Acad. Sci. (1973) 70(11):3240-3244.
Iborra, Francois, et al., "Kluyveromyces marxianus Small DNA Fragments Contain Both Autonomous Replicative and Centromeric Elements that also Function in Kluyveromyces lactis," Yeast 1994) 10:1621-1629.
Imai, Yuji, et al., "High-frequency Transformation of *Saccharomyces cerevisiae* with Linear Deoxyribonucleic Acid," Agric. Biol. Chem. (1980) 47(4):915-918.
Marykwas, Donna L., et al., "Mapping by multifragment cloning in vivo," Proc. Natl. Acad. Sci. (1995) 92:11701-11705.
Nonklang, Sanom, et al., "High-Temperature Ethanol Fermentation and Transformation with Linear DNA in the Thermotolerant Yeast *Kluyveromyces marxianus*," Applied and Environmental Microbiology (2008) 7514-7521.
Oldenburg, Kevin, et al., "Recombination-mediated PCR-directed plasmid construction in vivo in yeast," Nucleic Acids Research (1997) 25(2):451-452.
Yu, Daiguan, et al., "An efficient recombination system for chromosome engineering in *Escherichia coli*," Proc. Natl. Acad. Sci. (2003) 97(11)5978-5983.
Zhang, Youming, et al., "A new logic for DNA engineering using recombination in *Escherichia coli*," Nature Genetics (1998) 20:123-128.

*Primary Examiner* — Nancy T Vogel
(74) *Attorney, Agent, or Firm* — Chainey P. Singleton; Edwin S. Flores; Chalker Flores, LLP

(57) ABSTRACT

An object to be solved by the present invention is to provide, for example, a method for producing a *Kluyveromyces marxianus* transformant by a method for conveniently and efficiently connecting the ends of DNA fragments without using specific restriction enzymes or their recognition sequences, and a method for producing a useful substance using the transformant. The present inventors have found, as means to solve the object, a method comprising introducing two or more linear double-stranded DNA fragments free from a *Kluyveromyces marxianus* autonomously replicating sequence into *Kluyveromyces marxianus* and selecting a transformant comprising a desired DNA ligation product with marker gene expression by the desired DNA ligation product as an index, or comprising introducing a linear double-stranded DNA fragment comprising a *Kluyveromyces marxianus* autonomously replicating sequence, alone or in combination with one or more linear double-stranded DNA fragment(s) different therefrom into *Kluyveromyces marxianus* and selecting a transformant comprising a desired circular DNA ligation product with marker gene expression by the desired circular DNA ligation product as an index.

19 Claims, 13 Drawing Sheets

Figure 2

| PCR-synthesized fragment | The number of colonies(/10 pM DNA) |
|---|---|
| URA3-290 → [URA3 gene] ← URA3-280c | 242, 306, 276 |
| URA3-290 → [URA3 gene] ← URA3+771c    URA3+772 → [ ] ← URA3-280c | 30, 45, 33 |
| URA3-290 → [URA3 gene] ← URA3+771c | 0, 0, 0 |
| URA3+772 → [ ] ← URA3-280c | 0, 0, 0 |

Results of three transformation experiments are shown.

| PCR-synthesized fragment | The number of colonies |
|---|---|
|  | 327 |
|  | 243 |
|  | 130 |
|  | 95 |

Figure 5

| PCR-synthesized fragment | The number of colonies |
|---|---|
| URA3-290 / URA3-280c, URA3 gene | 329 |
| URA3-290, URA3+771c, URA3+772, URA3-280c, URA3 gene | 182 |
| URA3-290, URA3+771c, URA3+773, URA3-280c, URA3 gene | 4 |
| URA3-290, URA3+771c, URA3+774, URA3-280c, URA3 gene | 1 |
| URA3-290, URA3+771c, URA3+770, URA3-280c, URA3 gene | 28 |
| URA3-290, URA3+771c, URA3+771, URA3-280c, URA3 gene | 21 |

Colonies may be formed with a slightly incorrect sequence.

METHOD FOR PRODUCING KLUYVEROMYCES MARXIANUS TRANSFORMANT

TECHNICAL FIELD

The present invention relates to, for example, a method for producing a *Kluyveromyces marxianus* transformant and a method for producing a useful substance using the transformant.

BACKGROUND ART

The technique of connecting the ends of DNA fragments to prepare arbitrary DNA molecules is a basic technique essential for many experimental procedures in the molecular biological field, including cloning. A current approach most generally used for ligating DNA fragments involves binding blunt-ended DNA molecules or DNA molecules complementary to each other at their sticky ends using DNA ligase. Also, the Cohen-Boyer method (see non-patent document 1) is known as a cloning method based on this approach. This method involves cleaving insert DNA and a vector with their respective restriction enzymes, purifying the fragments, and then ligating the fragments using DNA ligase to prepare the construct of interest, with which *E. coli* is then transformed, followed by amplification. Since such a DNA ligation method using restriction enzymes and DNA ligase, however, achieves ligation only between DNA molecules prepared in advance to have corresponding ends, the Cohen-Boyer method requires complicated in vitro procedures such as PCR and restriction enzyme treatment for preparing constructs for transformation and further requires a lot of time for selecting *E. coli* comprising the construct of interest from among colonies of transformed *E. coli*. For these reasons, the development of more convenient and efficient methods for ligating DNA molecules has been demanded.

In vitro and in vivo homologous recombination methods have been developed as cloning methods using neither restriction enzymes nor DNA ligase as a substitute for the Cohen-Boyer method. The in vitro homologous recombination method connects DNA molecules using specific recombinase and its recognition sequence. For example, the Gateway method of Invitrogen Corp. and the In-Fusion cloning method of Takara Bio Inc. are known. These methods, however, require particular DNA sequences present in both ends of insert DNA and in vectors and therefore, are not excellent in versatility. Alternatively, the known in vivo homologous recombination method uses *E. coli* (see non-patent documents 2 and 3) or bakery yeast (see non-patent documents 4 and 5). These in vivo homologous recombination methods are based on the fact that *E. coli* strains caused to express a plurality of phage-derived proteins, or bakery yeast has exceedingly high homologous recombination proficiency. Specifically, insert DNA having, at both ends, additional sequences homologous to a cloning vector and a cloning vector from which a homologous recombination site has been cleaved off with restriction enzymes or the like are prepared, and *E. coli* or bakery yeast can be transformed therewith to thereby obtain an insert DNA-integrated cloning vector as a result of homologous recombination within the transformed cell (in vivo). This reaction takes place independently of restriction enzyme sites and therefore allows insertion of a DNA fragment to various positions in a vector sequence. Another feature thereof is that cloning efficiency does not vary depending on the length of insert DNA. Both of these methods, however, utilize homologous recombination and thus require adding a sequence homologous to a vector to insert DNA. The in vivo homologous recombination method using *E. coli* further requires electroporation for obtaining high transformation efficiency and disadvantageously requires, for example, expensive apparatuses or instruments for the procedures. Alternatively, the in vivo homologous recombination method using bakery yeast requires bakery yeast-*E. coli* shuttle vectors used for transferring cloning vectors to *E. coli* in the large-scale preparation of DNA. Unfortunately, bakery yeast-*E. coli* shuttle vectors are not generally used and require time and effort for their preparation.

Alternatively, a known method for constructing and amplifying circular DNA without using restriction enzymes or DNA ligase involves transforming prokaryotic cells with linear DNA obtained by the rolling circle amplification method and reconstructing circular DNA within the transformed cells (see patent document 1). The amplified DNA fragment prepared by the rolling circle amplification method, however, has a specific structure comprising repeating sequences. It is uncertain whether this method can be applied to the circularization of a DNA fragment free from repeating sequences.

PRIOR ART DOCUMENTS

Patent Documents

Patent Document 1: Japanese unexamined Patent Application Publication No. 2005-229950

Non-Patent Documents

Non-patent Document 1: Cohen S N et al., Proc Natl Acad Sci USA. 70, 3240-3244 (1973)
Non-patent Document 2: Zhang Y et al., Nat Genet. 20, 123-128 (1998)
Non-patent Document 3: Yu D et al., Proc Natl Acad Sci USA. 97, 5978-5983 (2000)
Non-patent Document 4: Marykwas D L and Passmore S E, Proc Natl Acad Sci USA. 92, 11701-11705 (1995)
Non-patent Document 5: Oldenburg K R et al., Nucleic Acids Res. 25, 451-452 (1997)

SUMMARY OF THE INVENTION

Object to be Solved by the Invention

An object of the present invention is to provide, for example, a method for producing a *Kluyveromyces marxianus* transformant by conveniently and efficiently connecting the ends of DNA fragments without using specific restriction enzymes or their recognition sequences, and a method for producing a useful substance using the transformant.

Means to Solve the Object

The present inventors have previously revealed that *Kluyveromyces marxianus*, a yeast species, has various excellent properties that are not observed in other yeasts (PCT/JP2007/001270 and PCT/JP2009/001214). During the course of research on *Kluyveromyces marxianus* transformation methods, it has been further suggested that linear DNA free from a homologous sequence is efficiently integrated into the genomic DNA of *Kluyveromyces marxianus* (Nonklang S. et al. Appl Environ Microbiol 74: 7514-7521

(2008)). From these findings, the present inventors have thought that *Kluyveromyces marxianus* can be used as a novel tool for molecular biological research, and attempted to develop a novel method for binding DNA fragments using *Kluyveromyces marxianus*. First, the present inventors have introduced a DNA fragment comprising a sequence from A in the transcriptional start codon ATG to +771 in the URA3 gene and a DNA fragment comprising a sequence from +772 to the stop codon in the URA3 gene into an uracil auxotrophic genetic mutant *Kluyveromyces marxianus* RAK3605 and cultured the strain in an uracil-deficient medium. As a result, it has been shown that a transformant comprising, in its genomic DNA, a DNA ligation product in which the introduced DNA fragments are connected can be efficiently obtained. In an attempt to identify the previously unknown autonomously replicating sequence (ARS) of *Kluyveromyces marxianus*, the present inventors have further determined the novel ARS sequences represented by SEQ ID NOs: 1 to 5 and found that a linear DNA fragment comprising any of these ARS sequences can be introduced into *Kluyveromyces marxianus* to thereby prepare a circular DNA ligation product. Based on these findings, the present invention has been completed.

Specifically, the present invention relates to (1) a method for producing a transformed yeast comprising a DNA ligation product consisting of two or more linear double-stranded DNA fragments, the method sequentially comprising the following steps (a) and (b):
(a) introducing two or more linear double-stranded DNA fragments free from an autonomously replicating sequence into *Kluyveromyces marxianus*, wherein the two or more linear double-stranded DNA fragments are two or more linear double-stranded DNA fragments, each of which does not comprise in itself a whole sequence necessary for marker gene expression and comprises a sequence that enables marker gene expression only when plural double-stranded DNA fragments are linked to form a desired DNA ligation product; and
(b) selecting a transformant with the desired DNA ligation product integrated in the genomic DNA obtained by the step (a) by using the marker gene expression as an index, (2) a method for producing a transformed yeast comprising a circular DNA ligation product consisting of one linear double-stranded DNA fragment, the method sequentially comprising the following steps (a) and (b):
(a) introducing one linear double-stranded DNA fragment comprising a whole autonomously replicating sequence and a whole sequence necessary for marker gene expression into *Kluyveromyces marxianus*; and
(b) selecting the desired circular DNA ligation product obtained by the step (a) by using the marker gene expression as an index, (3) a method for producing a transformed yeast comprising a circular DNA ligation product consisting of two or more linear double-stranded DNA fragments, the method sequentially comprising the following steps (a) and (b):
(a) introducing a linear double-stranded DNA fragment comprising a whole autonomously replicating sequence and a portion of a sequence necessary for marker gene expression, in combination with one or more linear double-stranded DNA fragment(s) different therefrom into *Kluyveromyces marxianus*, wherein the one or more linear double-stranded DNA fragment(s) different therefrom is a linear double-stranded DNA fragment(s), each of which does not comprise in itself the whole sequence necessary for marker gene expression and comprises a sequence that enables marker gene expression only when linked with a linear double-stranded DNA fragment comprising the autonomously replicating sequence and a portion of the marker gene to form a desired circular DNA ligation product; and
(b) selecting a transformant comprising the desired circular DNA ligation product obtained by the step (a) by using the marker gene expression as an index; (4) a method for producing a transformed yeast comprising a circular DNA ligation product consisting of two or more linear double-stranded DNA fragments, the method sequentially comprising the following steps (a) and (b):
(a) introducing a linear double-stranded DNA fragment comprising a portion of autonomously replicating sequence and a portion of a sequence necessary for marker gene expression, in combination with one or more linear double-stranded DNA fragment(s) different therefrom into *Kluyveromyces marxianus*, wherein the one or more linear double-stranded DNA fragment(s) different therefrom is linear double-stranded DNA fragment(s), each of which does not comprises in itself a whole autonomously replicating sequence and a whole sequence necessary for marker gene expression, and comprises a sequence that forms the whole autonomously replicating sequence and a sequence that enables marker gene expression only when linked with a linear double-stranded DNA fragment comprising the portion of autonomously replicating sequence and the portion of the sequence necessary for marker gene expression to form a desired circular DNA ligation product; and
(b) selecting a transformant comprising the desired circular DNA ligation product obtained by the step (a) by using the marker gene expression as an index, (5) the production method according to any one of (2) to (4), wherein the autonomously replicating sequence comprises a nucleotide sequence represented by any of SEQ ID NOs: 1 to 5, (6) the production method according to any one of (1) to (5), wherein the DNA ligation product further comprises a gene encoding a desired useful substance, (7) the production method according to any one of (1) to (6), wherein *Kluyveromyces marxianus* is *Kluyveromyces marxianus* RAK3605, and the marker gene is URA3 gene, (8) a transformed yeast obtained by a production method according to (6) or (7), (9) a method for producing a useful substance, comprising culturing a transformed yeast according to (8) in a medium and collecting a desired useful substance from the cultures, and (10) a *Kluyveromyces marxianus* ARS sequence represented by any of SEQ ID NOs: 1 to 5.

Effect of the Invention

According to the present invention, a *Kluyveromyces marxianus* transformant with a ligation product of two or more linear DNA fragments integrated in the genomic DNA can be produced without using specific restriction enzymes or their recognition sequences. Moreover, according to the present invention, *Kluyveromyces marxianus* can be transformed with a desired DNA sequence having an additional sequence encoding *Kluyveromyces marxianus* ARS to thereby construct a circular DNA ligation product comprising the DNA sequence. As a result, the desired DNA sequence can be cloned without complicated procedures.

BRIEF DESCRIPTION OF DRAWINGS

FIG. 2 is a diagram showing results of preparing a DNA ligation product encoding URA3 by the method of the present invention.

FIG. 5 is a diagram showing results of preparing a DNA ligation product encoding URA3 by the method of the present invention.

MODE OF CARRYING OUT THE INVENTION

Figure 1:
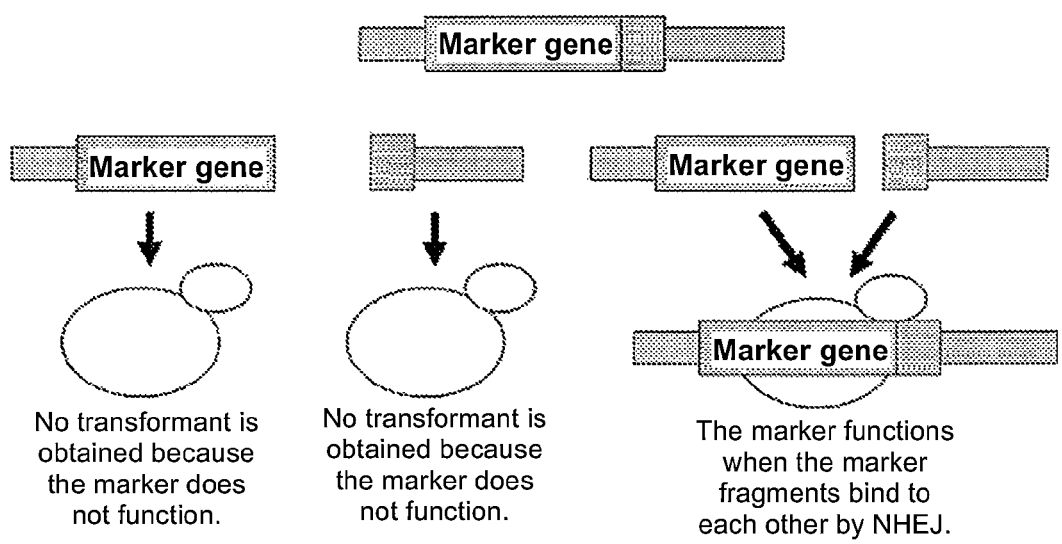
FIG. 1 is a diagram showing the summary of the method of the present invention for preparing a DNA ligation product using two linear double-stranded DNA fragments.

The method of the present invention for producing a transformed yeast comprising a DNA ligation product consisting of two or more linear double-stranded DNA fragments is not particularly limited as long as the method comprises the following steps (a) and (b) in order: (a) introducing two or more linear double-stranded DNA fragments free from an autonomously replicating sequence into *Kluyveromyces marxianus*, wherein the two or more linear double-stranded DNA fragments are two or more linear double-stranded DNA fragments, each of which does not comprise in itself the whole sequence necessary for marker gene expression and comprises a sequence that permits marker gene expression only when forming a desired DNA ligation product by the ligation of the double-stranded DNA fragments; and (b) selecting, with the marker gene expression as an index, a transformant with the desired DNA ligation product integrated in the genomic DNA obtained by the step (a) (hereinafter, this method is also referred to as "production method [I]"). In this context, the "two or more linear double-stranded DNA fragments free from an autonomously replicating sequence" mean double-stranded DNA fragments, each of which does not comprise an autonomously replicating sequence and forms a DNA conjugate by its ligation with the other DNA fragment(s) in any order so that the resulting DNA conjugate does not comprise the autonomously replicating sequence. The "two or more linear double-stranded DNA fragments, each of which comprises a sequence that permits marker gene expression only when forming a desired DNA ligation product" mean linear double-stranded DNA fragments, each of which comprises a portion of a sequence necessary for marker gene expression within *Kluyveromyces marxianus*, but not the whole sequence necessary for marker gene expression within *Kluyveromyces marxianus*, and comprises a sequence that permits marker gene expression within *Kluyveromyces marxianus* only when forming a desired DNA ligation product by the ligation of the double-stranded DNA fragments in a desired order, but does not permit marker gene expression within *Kluyveromyces marxianus* when forming a DNA ligation product different from the desired DNA ligation product by the ligation of the double-stranded DNA fragments in an order different from the desired order.

The two or more linear double-stranded DNA fragments used in the production method [I] of the present invention are not particularly limited by their sequences, lengths, or terminal shapes, and may further comprise DNA of an arbitrary sequence in addition to arbitrary gene DNA targeted by cloning such as a gene encoding a desired useful substance, or arbitrary gene DNA such as a high-expression promoter-linked gene encoding a desired useful substance. For example, in the case where the desired DNA ligation product in the production method [I] of the present invention is a DNA ligation product comprising a high-expression promoter sequence, a marker gene-encoding sequence, and an arbitrary nucleotide sequence in order, the following combinations of two linear double-stranded DNA fragments exemplified in (i) or (ii) can be preferably used:

(i) a linear double-stranded DNA fragment comprising a high-expression promoter sequence and a marker gene-encoding sequence lacking its 3'-terminal region essential for functional marker gene expression, and a linear double-stranded DNA fragment comprising a sequence encoding the 3'-terminal region essential for functional marker gene expression and an arbitrary downstream nucleotide sequence such as a DNA sequence encoding the desired useful substance; and (ii) a linear double-stranded DNA fragment comprising a high-expression promoter sequence and a sequence encoding a 5'-terminal region comprising the transcription initiation site of a marker gene-encoding sequence, and a linear double-stranded DNA fragment that is free from the 5'-terminal region of the marker gene-encoding sequence and comprises the region of the marker gene-encoding sequence encoding the downstream region of the 5'-terminal region of the marker gene to the 3' end, and an arbitrary downstream nucleotide sequence such as a DNA sequence encoding the desired useful substance.

A method for preparing the linear double-stranded DNA fragments is not particularly limited as long as the method is known in the art for preparing linear double-stranded DNA fragments. Preferable examples thereof can include: methods for preparing relatively short double-stranded DNA fragments, such as a method involving annealing single strands synthesized by the phosphoramidite or phosphite method, and a preparation method based on usual PCR; and methods for preparing long DNA fragments, such as a preparation method based on fusion PCR (see Japanese unexamined Patent Application Publication No. 2009-268360). Among others, PCR is preferable. For example, in the case of using two or more linear double-stranded DNA fragments of (i) above in the production method [I] of the present invention, the "linear double-stranded DNA fragment comprising a high-expression promoter sequence and a marker gene-encoding sequence lacking its 3'-terminal region essential for functional marker gene expression" is prepared in advance by PCR, while another "linear double-stranded DNA fragment comprising a sequence encoding the 3'-terminal region essential for functional marker gene expression and an arbitrary downstream nucleotide sequence" can be prepared using a primer set corresponding to the arbitrary nucleotide sequence, i.e., a primer set consisting of a sense (forward) primer comprising the sequence encoding the 3'-terminal region essential for functional marker gene expression and a sequence encoding the 5'-terminal region of the arbitrary nucleotide sequence and an antisense (reverse) primer comprising a sequence complementary to the 3'-terminal region of the arbitrary nucleotide sequence to thereby easily prepare linear double-stranded DNA fragments comprising various arbitrary nucleotide sequences to which the common "sequence encoding the 3'-terminal region essential for functional marker gene expression" has been added. According to the production method [I] of the present invention, two or more linear double-stranded DNA fragments need only to be introduced directly into a yeast without being ligated. As a result, a desired DNA ligation product in which these linear double-stranded DNA fragments are ligated can be formed. The yeast transformed with the desired ligation product can be further cultured to thereby amplify the desired DNA ligation product. Thus, efficient gene cloning, for example, can be achieved.

The method of the present invention for producing a transformed yeast comprising a circular DNA ligation product consisting of one linear double-stranded DNA fragment is not particularly limited as long as the method comprises the following steps (a) and (b) in order: (a) introducing one linear double-stranded DNA fragment into *Kluyveromyces marxianus*, the one linear double-stranded DNA fragment comprising the whole autonomously replicating sequence and the whole sequence necessary for marker gene expression; and (b) selecting, with the marker gene expression as an index, the desired circular DNA ligation product obtained by the step (a) (hereinafter, this method is also referred to as "production method [II]"). The "one linear double-stranded DNA fragment comprising the whole autonomously replicating sequence and the whole sequence necessary for marker gene expression" used in the production method [II] is not particularly limited by its sequence, length, or terminal shape as long as the linear double-stranded DNA fragment comprises the whole autonomously replicating sequence that is functional within *Kluyveromyces marxianus* and comprises a sequence that permits marker gene expression within *Kluyveromyces marxianus*. The linear double-stranded DNA fragment may further comprise DNA of an arbitrary sequence in addition to arbitrary gene DNA targeted by cloning, such as a gene encoding a desired useful substance, or arbitrary gene DNA such as a high-expression promoter-linked gene encoding a desired useful substance. A method for preparing the linear double-stranded DNA fragment is not particularly limited as long as the method is known in the art for preparing linear double-stranded DNA fragments. Preferable examples thereof can include: methods for preparing relatively short double-stranded DNA fragments, such as a method involving annealing single strands synthesized by the phosphoramidite or phosphite method, and a preparation method based on usual PCR; and methods for preparing long DNA fragments, such as a preparation method based on fusion PCR (see Japanese unexamined Patent Application Publication No. 2009-268360). PCR using primers comprising the autonomously replicating sequence is particularly preferable. The desired circular DNA ligation product prepared by the production method [II] can be obtained using a circular DNA extraction method known in the art from the transformant selected by the step (b) of the production method [II]. According to the production method [II] of the present invention, one linear double-stranded DNA fragment comprising the autonomously replicating sequence needs only to be introduced directly into a yeast without being self-ligated. As a result, a desired circular DNA ligation product can be formed. The yeast transformed with the desired circular DNA ligation product can be further cultured to thereby amplify the desired circular DNA ligation product.

The method of the present invention for producing a transformed yeast comprising a circular DNA ligation product consisting of two or more linear double-stranded DNA fragments is not particularly limited as long as the method comprises the following steps (a) and (b) in order: (a) introducing a linear double-stranded DNA fragment comprising the whole autonomously replicating sequence and a portion of a sequence necessary for marker gene expression, in combination with one or more linear double-stranded DNA fragment(s) different therefrom into *Kluyveromyces marxianus*, wherein the one or more linear double-stranded DNA fragment(s) different therefrom is linear double-stranded DNA fragment(s), each of which does not comprise in itself the whole sequence necessary for marker gene expression and comprises a sequence that permits marker gene expression only when forming a desired circular DNA ligation product by the ligation thereof with the linear double-stranded DNA fragment comprising the autonomously replicating sequence and a portion of the marker gene; and (b) selecting, with the marker gene expression as an index, a transformant comprising the desired circular DNA ligation product obtained by the step (a) (hereinafter, this method is also referred to as "production method [III]"), or comprises the following steps (a) and (b) in order: (a) introducing a linear double-stranded DNA fragment comprising a partial autonomously replicating sequence and a portion of a sequence necessary for marker gene expression, in combination with one or more linear double-stranded DNA fragment(s) different therefrom into *Kluyveromyces marxianus*, wherein the one or more linear double-stranded DNA fragment(s) different therefrom is linear double-stranded DNA fragment(s), each of which comprises in itself neither the whole autonomously replicating sequence nor the whole sequence necessary for marker gene expression and comprises a sequence that gives the whole autonomously replicating sequence and permits marker gene expression only when forming a desired circular DNA ligation product by the ligation thereof with the linear double-stranded DNA fragment comprising a partial autonomously replicating sequence and a portion of a sequence necessary for marker gene expression; and (b) selecting, with the marker gene expression as an index, a transformant comprising the desired circular DNA ligation product obtained by the step (a) (hereinafter, this method is also referred to as "production method [IV]"). The "linear double-stranded DNA fragment comprising the whole autonomously replicating sequence and a portion of a sequence necessary for marker gene expression" in the production method [III] is not particularly limited as long as the double-stranded DNA fragment comprises the whole autonomously replicating sequence that is functional within *Kluyveromyces marxianus* and does not comprise the whole sequence necessary for marker gene expression that is functional within *Kluyvero-*

*myces marxianus*. The "one or more linear double-stranded DNA fragment(s) different therefrom" in the production method [III] is not limited by its sequence, length, or terminal shape as long as the double-stranded DNA fragment(s) does not comprise in itself the whole sequence necessary for marker gene expression within *Kluyveromyces marxianus* and comprises a sequence that permits marker gene expression within *Kluyveromyces marxianus* only when forming a desired circular DNA ligation product. The "linear double-stranded DNA fragment comprising a partial autonomously replicating sequence and a portion of a sequence necessary for marker gene expression" in the production method [IV] is not particularly limited as long as the double-stranded DNA fragment comprises neither the whole autonomously replicating sequence that is functional within *Kluyveromyces marxianus* nor the whole sequence necessary for marker gene expression that is functional within *Kluyveromyces marxianus*. The "one or more linear double-stranded DNA fragment(s) different therefrom" in the production method [IV] is not limited by its sequence, length, or terminal shape as long as the double-stranded DNA fragment(s) comprises in itself neither the whole autonomously replicating sequence that is functional within *Kluyveromyces marxianus* nor the whole sequence necessary for marker gene expression and forms a desired DNA conjugate only by the ligation thereof with the "linear double-stranded DNA fragment comprising a partial autonomously replicating sequence and a portion of a sequence necessary for marker gene expression" so that the resulting DNA conjugate comprises the autonomously replicating sequence and the sequence necessary for marker gene expression.

The "linear double-stranded DNA fragment comprising the whole autonomously replicating sequence and a portion of a sequence necessary for marker gene expression" and the "one or more linear double-stranded DNA fragment(s) different therefrom" used in the production method [III] of the present invention may further comprise DNA of an arbitrary sequence in addition to arbitrary gene DNA targeted by cloning such as a gene encoding a desired useful substance, or arbitrary gene DNA such as a high-expression promoter-linked gene encoding a desired useful substance. Also, the "linear double-stranded DNA fragment comprising a partial autonomously replicating sequence and a portion of a sequence necessary for marker gene expression" and the "one or more linear double-stranded DNA fragment(s) different therefrom" used in the production method [IV] of the present invention may further comprise an arbitrary nucleotide sequence such as a nucleotide sequence comprising a gene sequence targeted by cloning or a nucleotide sequence comprising a high-expression promoter and an arbitrary gene sequence linked downstream thereof. A method for preparing the linear double-stranded DNA fragments is not particularly limited as long as the method is known in the art for preparing linear double-stranded DNA fragments. Preferable examples thereof can include: methods for preparing relatively short double-stranded DNA fragments, such as a method involving annealing single strands synthesized by the phosphoramidite or phosphite method, and a preparation method based on usual PCR; and methods for preparing long DNA fragments, such as a preparation method based on fusion PCR (see Japanese unexamined Patent Application Publication No. 2009-268360). PCR using primers comprising the autonomously replicating sequence is particularly preferable. The desired circular DNA ligation product prepared by the production method [III] or [IV] can be obtained using a circular DNA extraction method known in the art from the transformant selected by the step (b) of the production method [III] or [IV]. According to the production method [III] or [IV] of the present invention, one linear double-stranded DNA fragment comprising the whole or partial autonomously replicating sequence needs only to be introduced directly into a yeast without being ligated with the other fragment(s). As a result, a desired circular DNA ligation product can be formed. The yeast transformed with the desired circular DNA ligation product can be further cultured to thereby amplify the desired circular DNA ligation product.

In the production methods [I] to [IV] of the present invention, a method for introducing the linear double-stranded DNA fragment(s) into *Kluyveromyces marxianus* is not particularly limited as long as the method is an approach usually used for yeast transformation. Preferable examples thereof can include the lithium acetate method (J. Bacteriology, 153, p. 163 (1983); Proc. Natl. Acad. Sci. USA, 75, p. 1929 (1978); and Methods in yeast genetics, 2000 Edition: A Cold Spring Harbor Laboratory Course Manual), the electroporation method (Meth. Enzym., 194, p. 182 (1990)), and the spheroplast method (Proc. Natl. Acad. Sci. USA, 75, p. 1929 (1978)). Among them, the lithium acetate method can be advantageously used. The lithium acetate method, albeit very convenient, is known to have much lower transformation efficiency than that of other transformation methods. However, *Kluyveromyces marxianus* used in the present invention allows efficient transformation using linear double-stranded DNA fragments and thus, can achieve sufficient transformation efficiency even in the lithium acetate method.

The marker gene is not particularly limited as long as the marker gene can be used in yeasts. Preferable examples thereof can include auxotrophic marker genes complementing the auxotrophy of host *Kluyveromyces marxianus*, drug (e.g., antibiotic) resistance marker genes, genes encoding fluorescent proteins such as green fluorescent protein (GFP), and a gene encoding β-galactosidase. Among them, auxotrophic marker genes are preferable. The auxotrophic marker gene may be, for example, an auxotrophic marker gene complementing the auxotrophy of an amino acid (e.g., tryptophan, arginine, or leucine) auxotrophic mutant or an auxotrophic marker gene complementing the auxotrophy of a nucleic acid (e.g., adenine or uracil) auxotrophic mutant and is particularly preferably URA3 gene complementing the auxotrophy of an uracil auxotrophic mutant. In the present invention, two or more marker genes may be used in combination.

Likewise, the *Kluyveromyces marxianus* is not particularly limited and may be a wild-type strain or a mutant having genetic mutation, such as an auxotrophic mutant. The auxotrophic mutant is preferable because its transformant can be easily selected with auxotrophic marker gene expression as an index. Among others, a nucleic acid (e.g., adenine or uracil) auxotrophic mutant is particularly preferable. For example, in the case of using an uracil auxotrophic mutant of *Kluyveromyces marxianus* in the production methods [I] to [IV] of the present invention, its combination with the URA3 gene as a marker gene can achieve efficient selection of a transformant comprising the desired DNA ligation product. Alternatively, in the case of using an adenine auxotrophic mutant of *Kluyveromyces marxianus* therein, its combination with the ADE2 gene as a marker gene can achieve efficient selection of such a transformant. Preferable examples of the uracil auxotrophic mutant can specifically include *Kluyveromyces marxianus* RAK3605, *Kluyveromyces marxianus* RAK4071, *Kluyveromyces marxianus*

RAK4076, and *Kluyveromyces marxianus* RAK4077. Preferable examples of the adenine autotrophic mutant can specifically include RAK6038.

The autonomously replicating sequence used in the present invention is not particularly limited as long as the sequence serves as an autonomous replication origin in *Kluyveromyces marxianus*. The autonomously replicating sequence is preferably, for example, an autonomously replicating sequence KmARS7 (201-250) consisting of the nucleotide sequence represented by SEQ ID NO: 1 (5'-CAAGACTTCTTGAAGTGAAAACCAACTTTCAGTCT-TCAAACTAAAAATGA-3'), an autonomously replicating sequence KmARS11 (46-105) consisting of the nucleotide sequence represented by SEQ ID NO: 2 (5'-TCCAAAAT-TAACTTTCTAAGCTAAATGTCATATTTCG-CAATAAAATAATAAGAATATA GA-3'), an autonomously replicating sequence KmARS16 (721-790) consisting of the nucleotide sequence represented by SEQ ID NO: 3 (5'-TTTTATTTTTTTTAACTCAATTTCCAGTT-TAAACACCAAAATACGTTTCCATATAAT TGAAAAAGGAAG-3'), an autonomously replicating sequence KmARS18 (80-159) consisting of the nucleotide sequence represented by SEQ ID NO: 4 (5'-GATTAT-TATAAGGCATAATGCCAGGAATCTTTCCATAATTTG-GAATTGAAAGTCACTT TAGGTTCACTATATAAT-GAAAA-3'), an autonomously replicating sequence KmARS36 (291-340) consisting of the nucleotide sequence represented by SEQ ID NO: 5 (5'-TCTTTAATATT-ATTTTTCATTTCAAAAAGTGTGAAATAAAAAT-TAAAATG-3'), or an autonomously replicating sequence derived from the nucleotide sequence represented by any of SEQ ID NOs: 1 to 5 by the deletion, substitution, or addition of one or more base(s). The autonomously replicating sequence comprising the nucleotide sequence represented by any of SEQ ID NOs: 1 to 5 or the autonomously replicating sequence derived from the nucleotide sequence represented by any of SEQ ID NOs: 1 to 5 by the deletion, substitution, or addition of one or more base(s) can be added to an arbitrary DNA fragment by a method known in the art such as PCR to thereby prepare a linear double-stranded DNA fragment comprising the autonomously replicating sequence, which can in turn be used in the production methods [II] to [IV] of the present invention.

The method of the present invention for producing a useful substance is not particularly limited as long as the method comprises: culturing a yeast transformed with a DNA ligation product comprising a gene encoding a desired useful substance in a medium, the transformed yeast being obtained by any of the production methods [I] to [IV] of the present invention; and collecting the desired useful substance from the cultures. Preferable examples of the useful substance can include, but not particularly limited to, recombinant pharmaceutical proteins such as antibodies and cytokines. Since *Kluyveromyces marxianus* is a yeast having high protein productivity and heat resistance (Biosci. Biotechnol. Biochem. 71: 1170-82, 2007), the method of the present invention for producing a useful substance can achieve inexpensive and efficient production of the useful substance.

Examples of kits for production of DNA ligation products or circular DNA ligation products that can be usefully used in the method of the present invention for producing a transformed yeast can include those provided with *Kluyveromyces marxianus*. The *Kluyveromyces marxianus* may be a wild-type strain or a mutant having genetic mutation, such as an auxotrophic mutant and is preferably an auxotrophic mutant. Among others, a nucleic acid (e.g., adenine or uracil) auxotrophic mutant is particularly preferable. Preferable examples of the uracil auxotrophic mutant can specifically include *Kluyveromyces marxianus* RAK3605, and *Kluyveromyces marxianus* RAK4071, *Kluyveromyces marxianus* RAK4076, *Kluyveromyces marxianus* RAK4077. Preferable examples of the adenine autotrophic mutant can specifically include RAK6038. The uracil auxotrophic mutant *Kluyveromyces marxianus* RAK3605 is particularly preferable. The kit of the present invention for production of circular DNA ligation products may be further provided with a primer comprising the nucleotide sequence represented by any of SEQ ID NOs: 1 to 5, or a primer comprising an autonomously replicating sequence derived from the nucleotide sequence represented by any of SEQ ID NOs: 1 to 5 by the deletion, substitution, or addition of one or more base(s). Also, the kit may further comprise double-stranded DNA comprising the whole or a portion of a sequence encoding a marker gene, a medium for culture of *Kluyveromyces marxianus*, a buffer solution, etc.

Hereinafter, the present invention will be described more specifically with reference to Examples. However, the technical scope of the present invention is not intended to be limited to these Examples.

EXAMPLE 1

Preparation of DNA Ligation Product Encoding URA3

1. Preparation of DNA Fragments

PCR reaction was performed with *Saccharomyces cerevisiae* BY4704-derived DNA as a template using KOD-plus polymerase (manufactured by TOYOBO CO., LTD.) to prepare DNA fragments comprising the whole or a portion of the URA3 gene (URA3-290-280c, URA3-290+771c, and URA3+772-280c). The sequences of primers used in the PCR reaction are as shown below. The DNA fragment URA3-290-280c comprising the whole URA3 was prepared using a forward primer URA3-290 and a reverse primer URA3-280c; the DNA fragment URA3-290+771c comprising a portion (encoding the N-terminal region) of URA3 was prepared using a forward primer URA3-290 and a reverse primer URA3+771c; and the DNA fragment URA3+772-280c comprising a portion (encoding the C-terminal region) of URA3 was prepared using a forward primer URA3+772 and a reverse primer URA3-280c.

```
(Forward primer)
URA3-290
(5'-GAGAAGGGCAACGGTTCATCATCTC-3'; SEQ ID NO: 6)

URA3+772
(5'-GCATATTTGAGAAGATGCGGCCAGC-3'; SEQ ID NO: 7)

(Reverse primer)
URA3+771c
(5'-TTCCCAGCCTGCTTTTCTGTAACGT-3'; SEQ ID NO: 8)

URA3-280c
(5'-CAGTCTGTGAAACATCTTTCTACCA-3'; SEQ ID NO: 9)
```

The PCR reaction was performed by initial denaturation at 94° C. for 1 minute followed by 30 cycles each involving thermal denaturation at 94° C. for 20 seconds, annealing at 55° C. for 30 seconds, and elongation reaction at 68° C. for 2.5 minutes. The PCR reaction solution was prepared as shown below. After the reaction, the DNA concentration of each obtained PCR product was determined, and the concentration of each amplified DNA fragment was adjusted to 10 pM.
(Reaction Solution)

| Template | 0.4 µL |
|---|---|
| 10 x Buffer | 1.0 µL |
| 2 mM dNTPs | 1.0 µL |
| 25 mM MgSO₄ | 0.4 µL |
| Forward primer | 0.2 µL |
| Reverse primer | 0.2 µL |
| KOD-plus polymerase | 0.2 µL |
| Sterile water | 6.6 µL |

EXAMPLE 2

2. Preparation of Transformants

A *Kluyveromyces marxianus* RAK3605 strain having uracil auxotrophic genetic mutation was inoculated to 10 ml of a YPD medium (1% yeast extracts, 2% polypeptone, and 2% glucose) and cultured at 28° C. for 20 hours. The culture solution was collected, transferred to two 15-mL tubes, and centrifuged at 8000 rpm for 3 minutes. The supernatant was discarded, and 300 µL/tube of a solution for transformation [2000 µl of 60% PEG3350, 150 µL of 4 M lithium acetate, 300 µL of 1 M DTT, and 550 µL of sterile water] was added to the precipitated cells, followed by stirring with a vortex mixer. The solution was centrifuged again at 8000 rpm for 3 minutes, and the supernatant was discarded. 600 µL/tube of a solution for transformation was added to the precipitated cells, and the mixture was then dispensed in an amount of 100 µL/tube to 1.5-mL tubes. The DNA fragments (3 µL each of the fragments) prepared in Example 1 were added alone or in combination thereto and heat-treated at 47° C. for 15 minutes. 150 µL of sterile water was added thereto, and the cells were spread over an uracil-deficient medium and cultured at 28° C. for 3 days. The number of grown colonies was counted.

The experiment is summarized in FIG. 1, and the results of three transformation experiments are shown in FIG. 2. 275 colonies on average were obtained from transformation with the DNA fragment URA3-290-280c comprising the whole URA3. 36 colonies on average were obtained from transformation with the combination of the DNA fragment URA3-290+771c comprising a portion (encoding the N-terminal region) of URA3 and the DNA fragment URA3+772-280c comprising a portion (encoding the C-terminal region) of URA3. By contrast, use of the DNA fragment URA3-290+771c or URA3+772-280c alone produced no observable colony. These results demonstrated that the transformant to which URA3-290+771c and URA3+772-280c were introduced in combination expressed full-length URA3 protein as a result of the binding between these two DNA fragments.

EXAMPLE 3

Preparation of DNA Ligation Product Encoding URA3, TDH3p, and yCLuc

1. Preparation of DNA Fragments

PCR reaction was performed with *Saccharomyces cerevisiae* BY4704-derived DNA as a template using KOD-plus polymerase (manufactured by TOYOBO CO., LTD.) to prepare DNA fragments comprising the whole or a portion of the URA3 gene (URA3-290-280c, URA3-290+771c, and URA3+772-280c). The sequences of primers used in the PCR reaction are as shown below. The DNA fragment URA3-290-280c comprising the whole URA3 was prepared using a forward primer URA3-290 and a reverse primer URA3-280c; the DNA fragment URA3-290+771c comprising a portion (encoding the N-terminal region) of URA3 was prepared using a forward primer URA3-290 and a reverse primer URA3+771c; and the DNA fragment URA3+772-280c comprising a portion (encoding the C-terminal region) of URA3 was prepared using a forward primer URA3+772 and a reverse primer URA3-280c.

(Forward primer)
URA3-290
(5'-GAGAAGGGCAACGGTTCATCATCTC-3'; SEQ ID NO: 6)

URA3+772
(5'-GCATATTTGAGAAGATGCGGCCAGC-3'; SEQ ID NO: 7)

(Reverse primer)
URA3+771c
(5'-TTCCCAGCCTGCTTTTCTGTAACGT-3'; SEQ ID NO: 8)

URA3-280c
(5'-CAGTCTGTGAAACATCTTTCTACCA-3'; SEQ ID NO: 9)

Also, PCR reaction was performed with *Kluyveromyces marxianus* RAK4960 strain-derived DNA as a template using KOD-plus polymerase (manufactured by TOYOBO CO., LTD.) to prepare DNA fragments comprising a sequence encoding TDH3p and yCLuc (URA3+772TAA+1662c and URA3+772TAA+17+1662c). The sequences of primers used in the PCR reaction are as shown below. The DNA fragment URA3+772TAA+1662c was prepared using a forward primer URA3+772TAA-TDH-527 and a reverse primer yCLuc+1662c; and the DNA fragment URA3+772TAA+17+1662c was prepared using a forward primer URA3+772TAA+17-TDH-527 and a reverse primer yCLuc+1662c.

(Forward primer)
URA3+772TAA-TDH-527
(5'-GCATATTTGAGAAGATGCGGCCAGCAAAACTAAgctgtaacccgt acatgcccaa-3'; SEQ ID NO: 10)

URA3+772TAA+17-TDH-527
(5'-GCATATTTGAGAAGATGCGGCCAGCAAAACTAAaaaactgtatta taagtGCTGTAACCCGTACATGCCCAA-3'; SEQ ID NO: 11)

(Reverse primer)
yCLuc+1662c
(5'-CTACTTGCACTCATCTGGGACC-3'; SEQ ID NO: 12)

The PCR reaction was performed by initial denaturation at 94° C. for 1 minute followed by 30 cycles each involving thermal denaturation at 94° C. for 20 seconds, annealing at 55° C. for 30 seconds, and elongation reaction at 68° C. for 3 minutes. The PCR reaction solution was prepared as shown below. After the reaction, the DNA concentration of each obtained PCR product was determined, and the concentration of each amplified DNA fragment was adjusted to 10 pM.

(Reaction Solution)

| Template | 0.4 μL |
|---|---|
| 10 x Buffer | 1.0 μL |
| 2 mM dNTPs | 1.0 μL |
| 25 mM MgSO₄ | 0.4 μL |
| Forward primer | 0.2 μL |
| Reverse primer | 0.2 μL |
| KOD-plus polymerase | 0.2 μL |
| Sterile water | 6.6 μL |

EXAMPLE 4

2. Preparation of Transformants

A *Kluyveromyces marxianus* RAK3605 strain having uracil auxotrophic genetic mutation was inoculated to 2 ml of a YPD medium (1% yeast extracts, 2% polypeptone, and 2% glucose) and cultured overnight. 1.5 mL of the culture solution was collected, transferred to another tube, and centrifuged at 12000 rpm for 1 minute. The supernatant was discarded, and 200 μL/tube of a solution for transformation [2000 μl of 60% PEG3350, 150 μL of 4 M lithium acetate, 300 μL of 1 M DTT, and 550 μL of sterile water] was then added to the precipitated cells, followed by stirring with a vortex mixer. The solution was centrifuged again at 12000 rpm for 1 minute, and the supernatant was discarded. 50 μL of a solution for transformation and the combination of the DNA fragments (3 μL each of the DNA fragments) prepared in Example 3 were added to the precipitated cells, and the mixture was stirred with a vortex mixer and heat-treated at 47° C. for minutes. Then, 150 μL of sterile water was added thereto, and the cells were spread over an uracil-deficient medium and cultured at 28° C. for 3 days. The number of grown colonies was counted.

Figure 3:
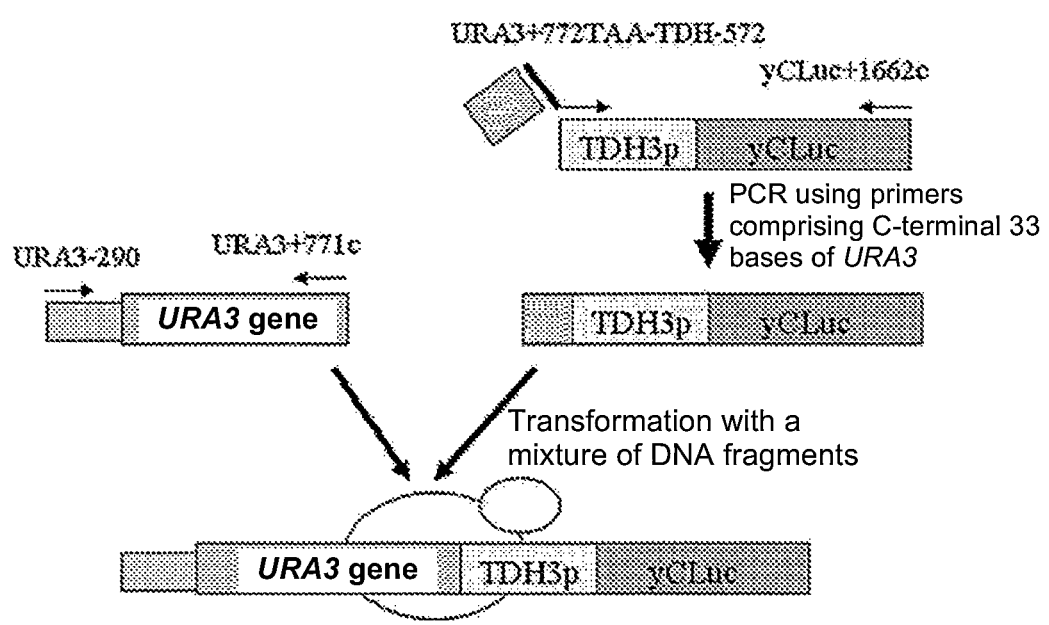
FIG. 3 is a diagram showing the summary of the method of the present invention for binding two linear double-stranded DNA fragments.
Figure 4:
FIG. 4 is a diagram showing results of preparing a DNA ligation product encoding URA3, TDH3p, and yCLuc by the method of the present invention.
Figure 4:
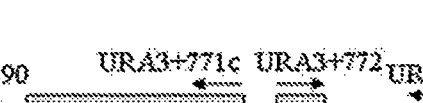
Figure 4:
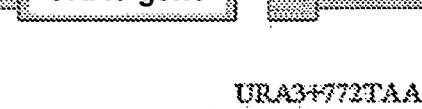
Figure 4:

The experiment is summarized in FIG. 3, and the results of the transformation experiment are shown in FIG. 4. 327 colonies were obtained from transformation with the DNA fragment URA3-290-280c comprising the whole URA3, while 243 colonies were obtained from transformation with the DNA fragment URA3-290+771c and the DNA fragment URA3+772-280c in combination. 130 colonies were obtained from transformation with the DNA fragment URA3-290+771c and the DNA fragment URA3+772TAA+1662c in combination, while 95 colonies were obtained from transformation with the DNA fragment URA3-290+771c and the DNA fragment URA3+772TAA+17+1662c in combination.

EXAMPLE 5

Preparation of DNA Ligation Product Consisting of DNA Fragments Having Partially Overlapping or Defective Sequences 1. Preparation of DNA Fragments PCR reaction was performed with *Saccharomyces cerevisiae* BY4704-derived DNA as a template using KOD-plus polymerase (manufactured by TOYOBO CO., LTD.) to prepare DNA fragments comprising the whole or a portion of the URA3 gene (URA3-290-280c, URA3-290+771c, URA3+772-280c, URA3+773-280c, URA3+774-280c, URA3+770-280c, and URA3+771-280c). The sequences of primers used in the PCR reaction are as shown below. The DNA fragment URA3-290-280c was prepared using a forward primer URA3-290 and a reverse primer URA3-280c; the DNA fragment URA3-290+771c was prepared using a forward primer URA3-290 and a reverse primer URA3+771c; the DNA fragment URA3+772-280c was prepared using a forward primer URA3+772 and a reverse primer URA3-280c; the DNA fragment URA3+773-280c was prepared using a forward primer URA3+773 and a reverse primer URA3-280c; the DNA fragment URA3+774-280c was prepared using a forward primer URA3+774 and a reverse primer URA3-280c; the DNA fragment URA3+770-280c was prepared using a forward primer URA3+770 and a reverse primer URA3-280c; and the DNA fragment URA3+771-280c was prepared using a forward primer URA3+771 and a reverse primer URA3-280c.

(Forward primer)
URA3-290
(5'-GAGAAGGGCAACGGTTCATCATCTC-3'; SEQ ID NO: 6)

URA3+772
(5'-GCATATTTGAGAAGATGCGGCCAGC-3'; SEQ ID NO: 7)

URA3+773
(5'-CATATTtGAGAAGATGCGGCCA-3'; SEQ ID NO: 13)

URA3+774
(5'-ATATTtGAGAAGATGCGGCCAG-3'; SEQ ID NO: 14)

URA3+770
(5'-AaGCATATTtGAGAAGATGCGG-3'; SEQ ID NO: 15)

URA3+771
(5'-aGCATATTtGAGAAGATGCGGC-3'; SEQ ID NO: 16)

(Reverse primer)
URA3+771c
(5'-TTCCCAGCCTGCTTTTCTGTAACGT-3'; SEQ ID NO: 8)

URA3-280c
(5'-CAGTCTGTGAAACATCTTTCTACCA-3'; SEQ ID NO: 9)

The PCR reaction was performed by initial denaturation at 94° C. for 1 minute followed by 30 cycles each involving thermal denaturation at 94° C. for 20 seconds, annealing at 55° C. for 30 seconds, and elongation reaction at 68° C. for 2.5 minutes. The PCR reaction solution was prepared as shown below. After the reaction, the DNA concentration of each obtained PCR product was determined, and the concentration of each amplified DNA fragment was adjusted to 10 pM.

(Reaction Solution)

| Template | 0.4 μL |
|---|---|
| 10 x Buffer | 1.0 μL |
| 2 mM dNTPs | 1.0 μL |
| 25 mM MgSO₄ | 0.4 μL |
| Forward primer | 0.2 μL |
| Reverse primer | 0.2 μL |
| KOD-plus polymerase | 0.2 μL |
| Sterile water | 6.6 μL |

EXAMPLE 6

2. Preparation of Transformants

A *Kluyveromyces marxianus* RAK3605 strain having uracil auxotrophic genetic mutation was inoculated to 2 ml of a YPD medium (1% yeast extracts, 2% polypeptone, and 2% glucose) and cultured overnight. 1.5 mL of the culture solution was collected, transferred to another tube, and centrifuged at 12000 rpm for 1 minute. The supernatant was discarded, and 200 μL/tube of a solution for transformation [2000 μl of 60% PEG3350, 150 μL of 4 M lithium acetate, 300 μL of 1 M DTT, and 550 μL of sterile water] was then added to the precipitated cells, followed by stirring with a vortex mixer. The solution was centrifuged again at 12000 rpm for 1 minute, and the supernatant was discarded. 50 μL of a solution for transformation and the combination of the DNA fragments (3 μL each of the DNA fragments) prepared in Example 5 were added to the precipitated cells, and the mixture was stirred with a vortex mixer and heat-treated at 47° C. for minutes. Then, 150 μL of sterile water was added thereto, and the cells were spread over an uracil-deficient medium and cultured at 28° C. for 3 days. The number of grown colonies was counted.

The results of the transformation experiment are shown in FIG. 5. 329 colonies were obtained from transformation with the DNA fragment URA3-290-280c comprising the whole URA3. 182 colonies were obtained from transformation with the combination of the DNA fragment URA3-290+771c comprising a portion (encoding the N-terminal region) of URA3 and the DNA fragment URA3+772-280c comprising a portion (encoding the C-terminal region) of URA3. Two combinations of the DNA fragment URA3-290+771c with the DNA fragment URA3+773-280c and the DNA fragment URA3-290+771c with the DNA fragment URA3+774-280c were combinations of the DNA fragments that formed a ligated sequence with in 1 or 2 base(s) defective in the URA3-encoding nucleotide sequence after the binding between the DNA fragments. Even such combinations were each confirmed to produce a small number of colonies (4 and 1 colonies, respectively). On the other hand, two combinations of the DNA fragment URA3-290+771c with the DNA fragment URA3+770-280c and the DNA fragment URA3-290+771c with the DNA fragment URA3+771-280c were combinations of the DNA fragments that formed a ligated sequence having a 1- or 2-base overlap in the URA3-encoding nucleotide sequence after the binding between the DNA fragments. As a result of such combinations, 28 and 21 colonies, respectively, were confirmed.

These results demonstrated that an N-terminal region-encoding DNA fragment of the URA3 gene and a DNA fragment provided on the 5' side with a C-terminal region-encoding of the URA3 gene could be prepared and introduced into a *Kluyveromyces marxianus RAK*3605 strain to thereby obtain a transformant comprising the DNA sequence of interest.

EXAMPLE 7

Identification of *Kluyveromyces marxianus* Autonomously Replicating Sequence

Figure 6:
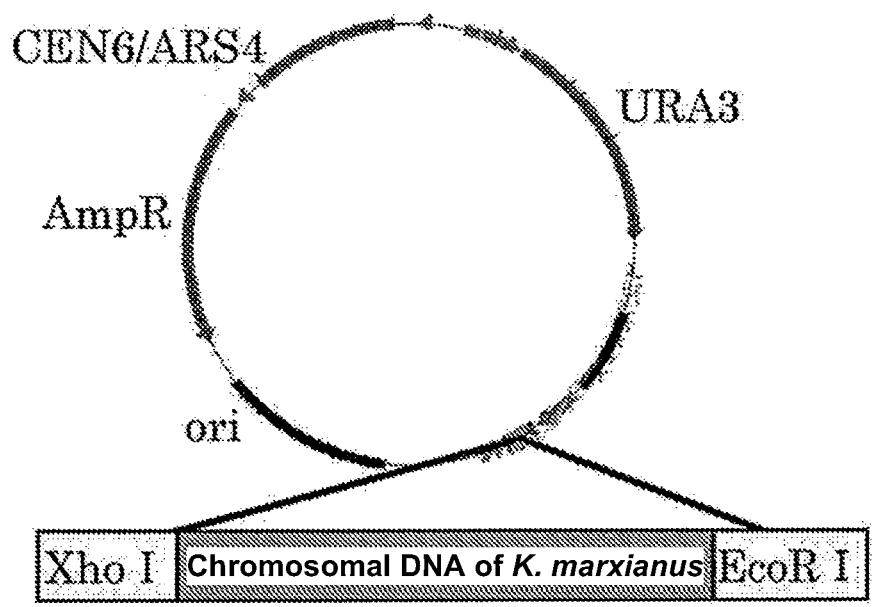
FIG. 6 is a diagram showing a plasmid used for obtaining the *Kluyveromyces marxianus* autonomously replicating sequence (KmARS) of the present invention.
Figure 7:
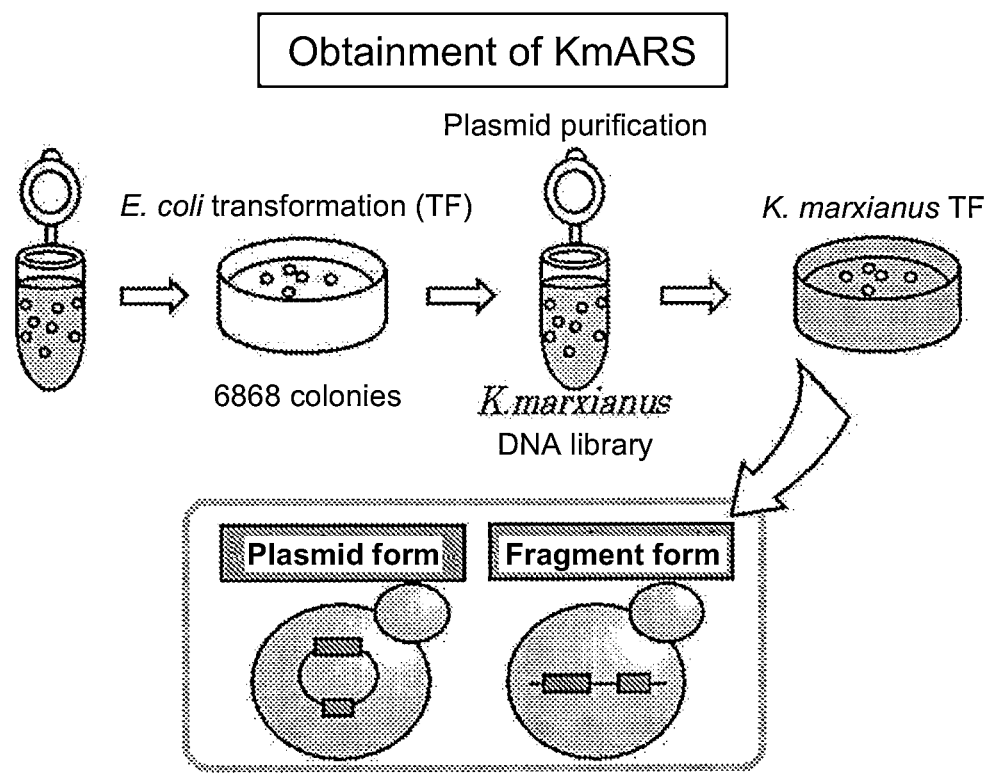
FIG. 7 is a diagram showing the summary of an experiment for obtaining the *Kluyveromyces marxianus* autonomously replicating sequence (KmARS) of the present invention.
Figure 8:
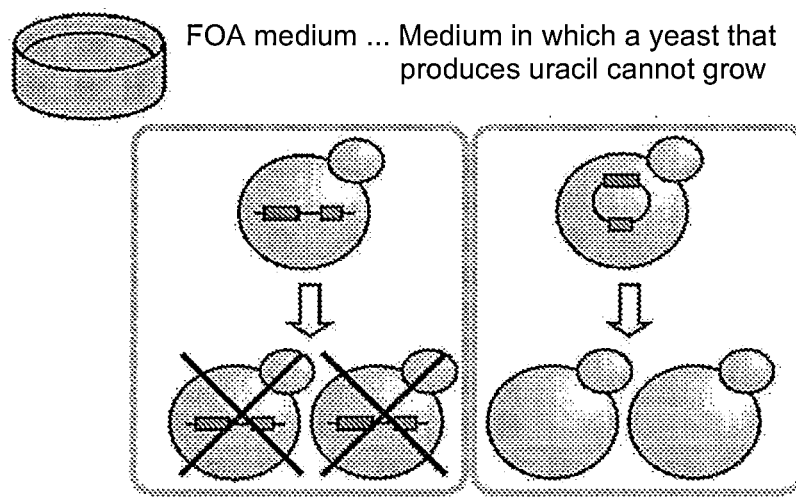
FIG. 8 is a diagram showing a method for selecting a transformant in order to obtain the *Kluyveromyces marxianus* autonomously replicating sequence (KmARS) of the present invention.

The following experiment was conducted for the purpose of identifying an autonomously replicating sequence (ARS) in *Kluyveromyces marxianus*: *Kluyveromyces marxianus*-derived genomic DNA was digested with restriction enzymes XhoI and EcoRI and inserted to a single-copy vector pRS316 for budding yeast (Sikorski and Hieter, 1989; Genetics 122, 19-27) (FIG. 6). This vector was introduced into *E. coli* to obtain 6868 colonies. Plasmids were extracted and purified from these colonies to prepare a *Kluyveromyces marxianus* genomic DNA library, which was then introduced into *Kluyveromyces marxianus* (FIG. 7). Strains in which URA3 was disrupted were selected using a 5-FOA medium to thereby select only transformed colonies having no genomic integration of the plasmid sequence (FIG. 8).

Figure 9:
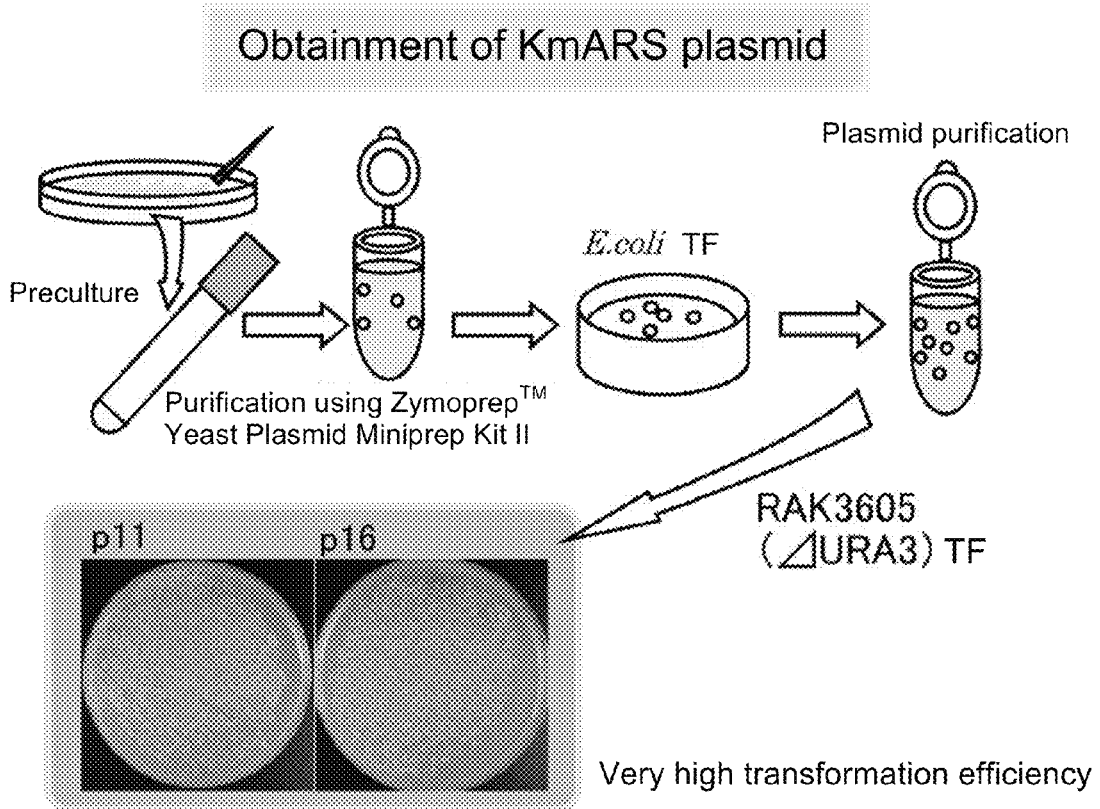
FIG. 9 is a diagram showing a method for obtaining a plasmid comprising the *Kluyveromyces marxianus* autonomously replicating sequence (KmARS) of the present invention.
Figure 10:
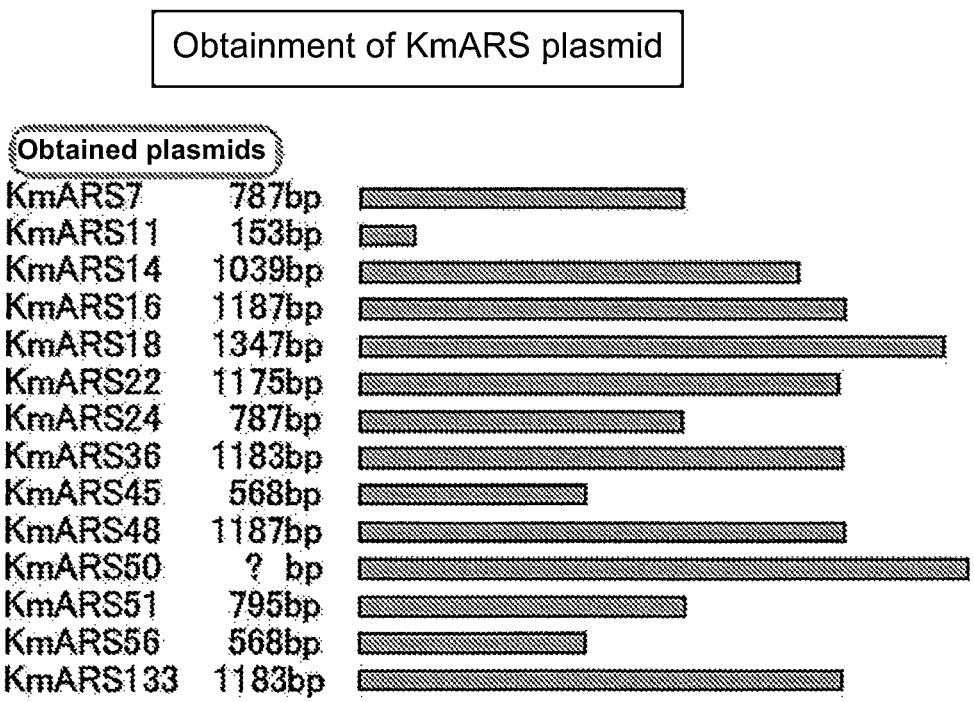
FIG. 10 is a diagram showing a plasmid comprising the *Kluyveromyces marxianus* autonomously replicating sequence (KmARS) of the present invention.

168 transformants thus obtained were cultured, and plasmids were purified using Zymoprep Yeast Plasmid Miniprep Kit II (manufactured by Zymo Research) and used in the transformation of *E. coli*. Plasmids were further extracted and purified from *E. coli* and used in the transformation of *Kluyveromyces marxianus* RAK3605 having uracil auxotrophic genetic mutation (FIG. 9). As a result, 14 types of plasmids were obtained as shown in FIG. 10. The sequence contained in the plasmid KmARS7 is shown in SEQ ID NO: 17; the sequence contained in the plasmid KmARS11 is shown in SEQ ID NO: 18; the sequence contained in the plasmid KmARS14 is shown in SEQ ID NO: 19; the sequence contained in the plasmid KmARS16 is shown in SEQ ID NO: 20; the sequence contained in the plasmid KmARS18 is shown in SEQ ID NO: 21; the sequence contained in the plasmid KmARS22 is shown in SEQ ID NO: 22; the sequence contained in the plasmid KmARS36 is shown in SEQ ID NO: 23; the sequence contained in the plasmid KmARS45 is shown in SEQ ID NO: 24; and the sequence contained in the plasmid KmARS51 is shown in SEQ ID NO: 25.

Figure 11:
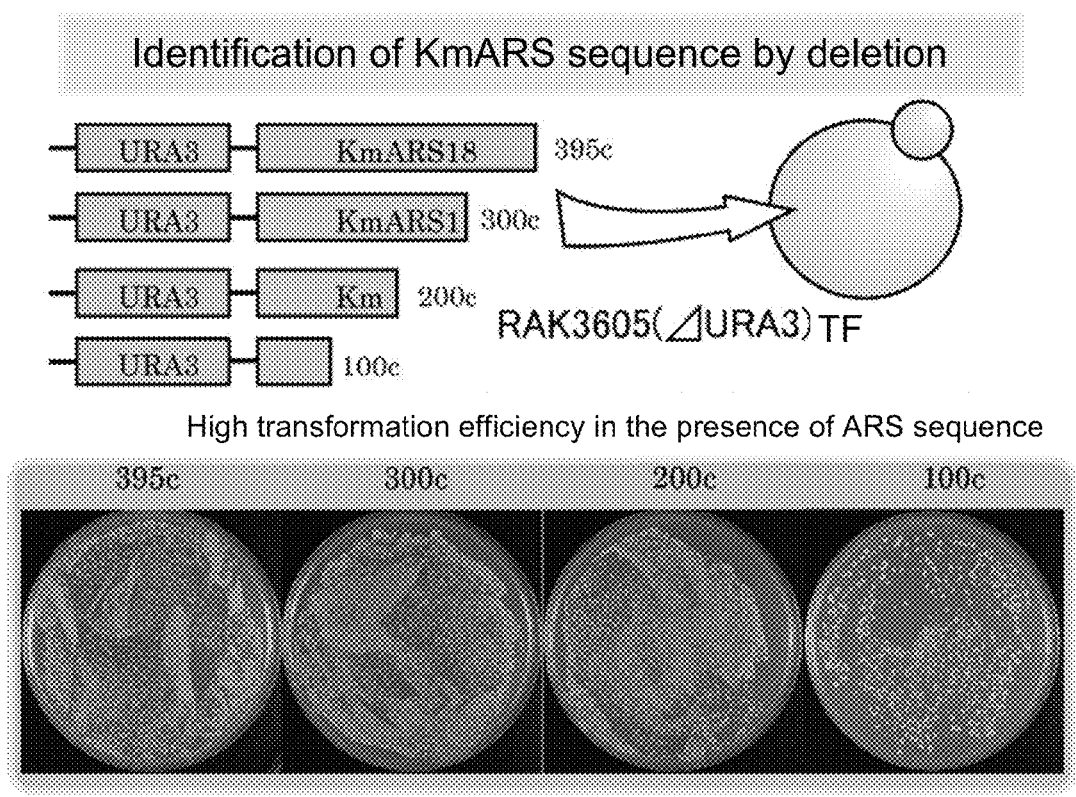
FIG. 11 is a diagram showing a deletion mutant for determining the *Kluyveromyces marxianus* autonomously replicating sequence (KmARS) of the present invention.
Figure 12:
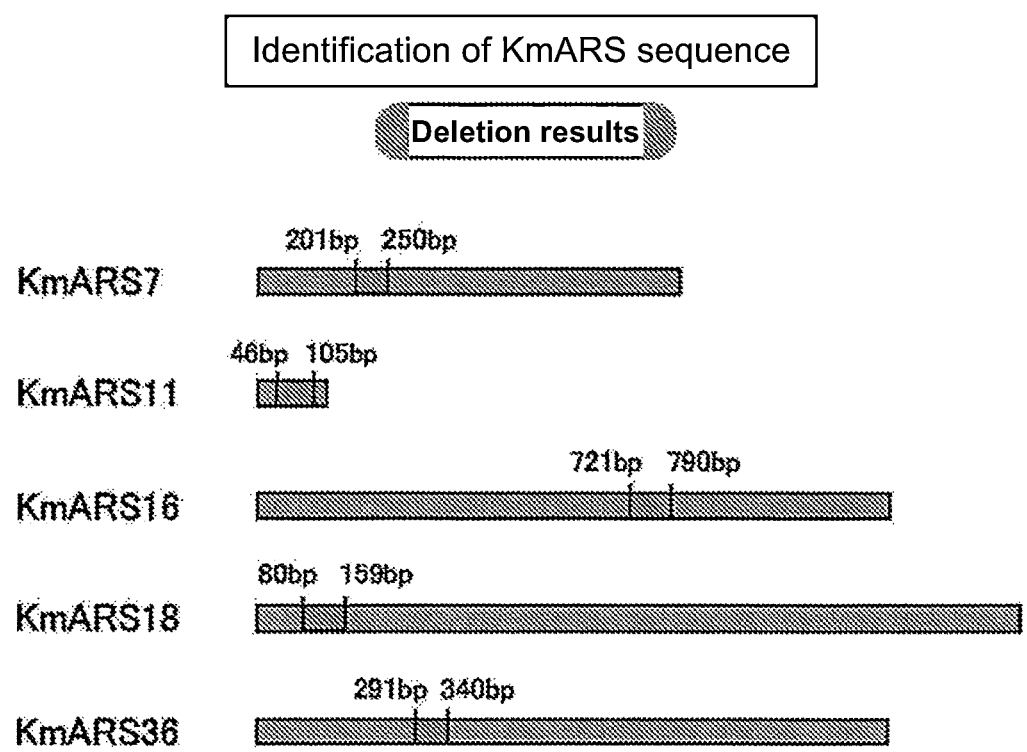
FIG. 12 is a diagram showing the *Kluyveromyces marxianus* autonomously replicating sequence (KmARS) of the present invention.

Subsequently, a deletion mutant was prepared and used in an experiment for the purpose of determining the KmARS region. The experiment is summarized in FIG. 11. From the results of the experiment shown in FIG. 12, KmARS was determined to be a region spanning KmARS7 205 to 250 bp (SEQ ID NO: 1), a region spanning KmARS11 46 to 105 bp (SEQ ID NO: 2), a region spanning KmARS16 721 to 700 bp (SEQ ID NO: 3), a region spanning KmARS7 80 to 159 bp (SEQ ID NO: 4), and a region spanning KmARS36 291 to 340 bp (SEQ ID NO: 5).

Figure 13:
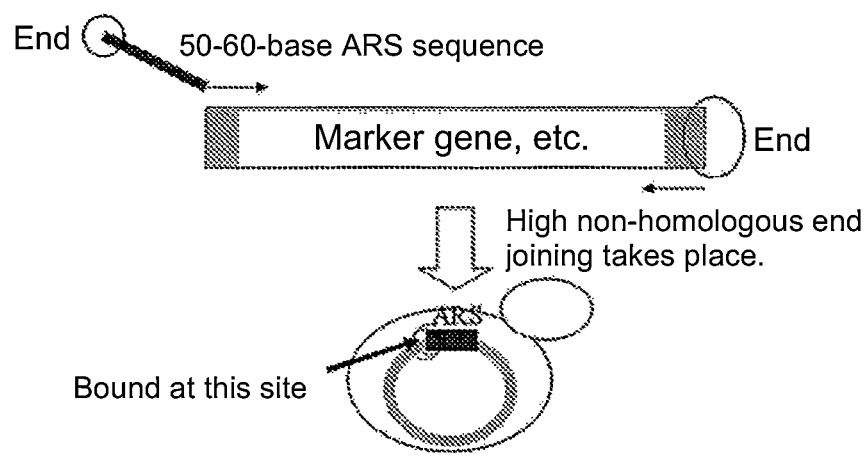
FIG. 13 is a diagram showing the summary of the method of the present invention for preparing a circular DNA ligation product.

These results demonstrated that, as shown in FIG. 13, the 50- to 60-bp KmARS identified this time could be added to an arbitrary DNA fragment and introduced into *Kluyveromyces marxianus* to thereby construct circular DNA within the transformed cell.

The invention claimed is:

1. A method for producing a transformed yeast comprising a DNA ligation product consisting of two or more linear double-stranded DNA fragments, wherein each of the two or more linear double-stranded DNA fragments does not comprise in itself a whole sequence necessary for marker gene expression and comprises a sequence that enables marker gene expression only when an end of plural double-stranded DNA fragments is linked by non-homologous end joining to form a desired DNA ligation product, the method sequentially comprising the following steps (a) and (b):
   (a) introducing the two or more linear double-stranded DNA fragments into *Kluyveromyces marxianus*; and
   (b) selecting a transformant with the desired DNA ligation product obtained by the step (a) by using the marker gene expression as an index.

2. The method-according to claim 1, wherein the two or more linear double-stranded DNA fragments are DNA fragments free from an autonomously replicating sequence, and the desired DNA ligation product is integrated in the genomic DNA.

3. The method according to claim 1, wherein one of the two or more linear double-stranded DNA fragments comprises a whole autonomously replicating sequence, and the desired DNA ligation product is circular.

4. The method according to claim 1, wherein the two or more linear double-stranded DNA fragments are DNA fragments that comprise a portion of the autonomously replicating sequence, each does not comprise in itself a whole autonomously replicating sequence, and comprise a sequence that enables expression of the whole autonomously replicating sequence only when an end of plural linear double-stranded DNA fragments is linked by non-homologous end joining, and that the desired DNA ligation product is circular.

5. The production method according to claim 3, wherein the autonomously replicating sequence comprises a nucleotide sequence represented by any of SEQ ID NOs: 1 to 5.

6. The production method according to claim 1, wherein the DNA ligation product further comprises a gene encoding a desired useful substance.

7. The production method according to claim 1, wherein *Kluyveromyces marxianus* is *Kluyveromyces marxianus* RAK3605, and the marker gene is URA3 gene.

8. The production method according to claim 4, wherein the autonomously replicating sequence comprises a nucleotide sequence represented by any of SEQ ID NOs: 1 to 5.

9. The production method according to claim 2, wherein the DNA ligation product further comprises a gene encoding a desired useful substance.

10. The production method according to claim 3, wherein the DNA ligation product further comprises a gene encoding a desired useful substance.

11. The production method according to claim 4, wherein the DNA ligation product further comprises a gene encoding a desired useful substance.

12. The production method according to claim 5, wherein the DNA ligation product further comprises a gene encoding a desired useful substance.

13. The production method according to claim 8, wherein the DNA ligation product further comprises a gene encoding a desired useful substance.

14. The production method according to claim 2, wherein *Kluyveromyces marxianus* is *Kluyveromyces marxianus* RAK3605, and the marker gene is URA3 gene.

15. The production method according to claim 3, wherein *Kluyveromyces marxianus* is *Kluyveromyces marxianus* RAK3605, and the marker gene is URA3 gene.

16. The production method according to claim 4, wherein *Kluyveromyces marxianus* is *Kluyveromyces marxianus* RAK3605, and the marker gene is URA3 gene.

17. The production method according to claim 5, wherein *Kluyveromyces marxianus* is *Kluyveromyces marxianus* RAK3605, and the marker gene is URA3 gene.

18. The production method according to claim 8, wherein *Kluyveromyces marxianus* is *Kluyveromyces marxianus* RAK3605, and the marker gene is URA3 gene.

19. The production method according to claim 6, wherein *Kluyveromyces marxianus* is *Kluyveromyces marxianus* RAK3605, and the marker gene is URA3 gene.

* * * * *

SEQUENCE LISTING

```
<160> NUMBER OF SEQ ID NOS: 25

<210> SEQ ID NO 1
<211> LENGTH: 50
<212> TYPE: DNA
<213> ORGANISM: Kluyveromyces marxianus
<220> FEATURE:
<223> OTHER INFORMATION: Inventor: Akada, Rinji
     Inventor: Hoshida, Hisashi
     Inventor: Abdel-Banat, Babiker Mohamed Ahmed
     Inventor: Asakawa, Jun
```

```
<400> SEQUENCE: 1
caagacttct tgaagtgaaa accaactttc agtcttcaaa ctaaaaatga              50

<210> SEQ ID NO 2
<211> LENGTH: 60
<212> TYPE: DNA
<213> ORGANISM: Kluyveromyces marxianus

<400> SEQUENCE: 2
tccaaaatta actttctaag ctaaatgtca tatttcgcaa taaataata agaatataga   60

<210> SEQ ID NO 3
<211> LENGTH: 70
<212> TYPE: DNA
<213> ORGANISM: Kluyveromyces marxianus

<400> SEQUENCE: 3
ttttattttt ttttaactca atttccagtt taaacaccaa aatacgtttc catataattg   60
aaaaaggaag                                                          70

<210> SEQ ID NO 4
<211> LENGTH: 80
<212> TYPE: DNA
<213> ORGANISM: Kluyveromyces marxianus

<400> SEQUENCE: 4
gattattata aggcataatg ccaggaatct ttccataatt tggaattgaa agtcacttta   60
ggttcactat ataatgaaaa                                               80

<210> SEQ ID NO 5
<211> LENGTH: 50
<212> TYPE: DNA
<213> ORGANISM: Kluyveromyces marxianus

<400> SEQUENCE: 5
tctttaatat tatttttcat ttcaaaaagt gtgaaataaa aattaaaatg              50

<210> SEQ ID NO 6
<211> LENGTH: 25
<212> TYPE: DNA
<213> ORGANISM: Artificial
<220> FEATURE:
<223> OTHER INFORMATION: URA3-290 forward primer

<400> SEQUENCE: 6
gagaagggca acggttcatc atctc                                         25

<210> SEQ ID NO 7
<211> LENGTH: 25
<212> TYPE: DNA
<213> ORGANISM: Artificial
<220> FEATURE:
<223> OTHER INFORMATION: URA3+772 forward primer

<400> SEQUENCE: 7
gcatatttga gaagatgcgg ccagc                                         25

<210> SEQ ID NO 8
<211> LENGTH: 25
<212> TYPE: DNA
<213> ORGANISM: Artificial
<220> FEATURE:
<223> OTHER INFORMATION: URA3+771c reverse primer
```

```
<400> SEQUENCE: 8
ttcccagcct gcttttctgt aacgt                                          25

<210> SEQ ID NO 9
<211> LENGTH: 25
<212> TYPE: DNA
<213> ORGANISM: Artificial
<220> FEATURE:
<223> OTHER INFORMATION: URA3-280c reverse primer

<400> SEQUENCE: 9
cagtctgtga acatctttc tacca                                           25

<210> SEQ ID NO 10
<211> LENGTH: 55
<212> TYPE: DNA
<213> ORGANISM: Artificial
<220> FEATURE:
<223> OTHER INFORMATION: URA3+772TAA-TDH-527 foward primer

<400> SEQUENCE: 10
gcatatttga gaagatgcgg ccagcaaaac taagctgtaa cccgtacatg cccaa         55

<210> SEQ ID NO 11
<211> LENGTH: 72
<212> TYPE: DNA
<213> ORGANISM: Artificial
<220> FEATURE:
<223> OTHER INFORMATION: URA3+772TAA+17-TDH-527 foward primer

<400> SEQUENCE: 11
gcatatttga gaagatgcgg ccagcaaaac taaaaaactg tattataagt gctgtaaccc    60
gtacatgccc aa                                                        72

<210> SEQ ID NO 12
<211> LENGTH: 22
<212> TYPE: DNA
<213> ORGANISM: Artificial
<220> FEATURE:
<223> OTHER INFORMATION: yCLuc+1662c reverse primer

<400> SEQUENCE: 12
ctacttgcac tcatctggga cc                                             22

<210> SEQ ID NO 13
<211> LENGTH: 22
<212> TYPE: DNA
<213> ORGANISM: Artificial
<220> FEATURE:
<223> OTHER INFORMATION: URA3+773 foward primer

<400> SEQUENCE: 13
catatttgag aagatgcggc ca                                             22

<210> SEQ ID NO 14
<211> LENGTH: 22
<212> TYPE: DNA
<213> ORGANISM: Artificial
<220> FEATURE:
<223> OTHER INFORMATION: URA3+774 foward primer

<400> SEQUENCE: 14
atatttgaga agatgcggcc ag                                             22
```

<210> SEQ ID NO 15
<211> LENGTH: 22
<212> TYPE: DNA
<213> ORGANISM: Artificial
<220> FEATURE:
<223> OTHER INFORMATION: URA3+770 foward primer

<400> SEQUENCE: 15
aagcatattt gagaagatgc gg                                        22

<210> SEQ ID NO 16
<211> LENGTH: 22
<212> TYPE: DNA
<213> ORGANISM: Artificial
<220> FEATURE:
<223> OTHER INFORMATION: URA3+771 foward primer

<400> SEQUENCE: 16
agcatatttg agaagatgcg gc                                        22

<210> SEQ ID NO 17
<211> LENGTH: 789
<212> TYPE: DNA
<213> ORGANISM: Kluyveromyces marxianus

<400> SEQUENCE: 17
ggaattcagg gatgatcttg agaagttctt agagtcttac gagggaacag aagatttgga    60
accagccaaa gctgctatag cggaagcaga tattttgcta agtaaatgat taaataatta   120
aatatgtgga aatacattaa tcttttttata tttttgcagt tcgttgtcgc tataattttat   180 agtcatctcg ttagttcaaa caagacttct tgaagtgaaa accaactttc agtcttcaaa   240
ctaaaaatga aaatcagtgg aagaaggtaa acgacttcat gttatatatg aattgaatag   300
taatggaaat aaccaaaaac agctcaacag aaaacaaaca aaatacgtta agacctgaac   360
tcctagcaga accataactg ccaaatattt attatctgtg gagatcttat attctaaaac   420
caaaaaaaat ataacttaaa agttaaaaag aagatgttct aactgaggtt cgaactcagg   480
acctttgccg tgtgaaggca acgtgatagc cactacacta ttagaactac cttatgggaa   540
aaagaaaaat agagtacaac tagaatggta agatctgtga cctttctaa acacttaatt   600 ccatatagac agttcccacc caccataagg tcacaattat aatgtcttta gaagaccact   660
gtcgttcatc atcttcctaa gccctctctc taaagcggca tatttccgta atttgttctt   720
ctttgcacag gcacgtgaga tgactccgat tattcccaca tgcatattta gcctctctag   780
gggctcgag                                                         789

<210> SEQ ID NO 18
<211> LENGTH: 153
<212> TYPE: DNA
<213> ORGANISM: Kluyveromyces marxianus

<400> SEQUENCE: 18
gaattcccaa aatcaatgat tcatacactt tttacactgt gacgttccaa aattaacttt    60
ctaagctaaa tgtcatattt cgcaataaaa taataagaat atagatatca aaggtctgtg   120
aagcttttat ttacactaat agatattctc gag                               153

<210> SEQ ID NO 19
<211> LENGTH: 1040
<212> TYPE: DNA
<213> ORGANISM: Kluyveromyces marxianus

<400> SEQUENCE: 19

```
gaattctctc tctctctctc ttcttttcc gttcccattt ccaaggtttg ccgttttttg      60
cggaatccga attggaacct gaacctgaac ctgaacctga acctgaatat gaaatctgag     120
tctgagtgag ttcaaatctg aatgcaactg caatcatccg caggcgcact tgacaatacc    180
cctcccaact tcattatata gatgtacttt tttaggtcta taaaaaatct ccatccattt    240
cagtacatag tacatacttt atcttttgcg tcatcgaaat actagaaaat aaaaaaatac    300
catatcacac ctatttcctc ttttctctct gtccaagcac atttggttat cgaaagctgt    360
caatgagctt acaatttgta attacatata tgtatcacat acacaagtac accaaaaaaa    420
aaggccccac aatagcaggg aaaaatattt acatacacac acactctcgc aacaacccac    480
cacgccccac cagggcccgc cacaacaccg gcaacaaccc tgtaaccgcc gcctcttcc     540
ttcctcctct ccctcatcac tctatacgtt ttgatctctc gaatttccag cttaaagctt    600
tgaaaatata atgattcttt taaacatagg aaaaagtag aaaaaactaa caacttgggc     660
gcatgtaata aagaacacga aaagacaac aaaatatagc cactacaaga gccaaacaca     720
ggggaaataa cggaactaac agagccaatt gaagctctaa aatctgaaat ctaaagtttc    780
aaatcgggaa attgtattag agagttgatt ttccgcccctt tctttcgtgt aaaggactcc    840
agattagata gatgcttaca gattatcagc ggtccgatgc cgcttccatt ctgcccacgg    900
tggagagatt atttgctgaa ggagtgttta agaaatattt gaatccgagc caattgcttc    960
ttttgaagtc gctactgcac cttcgtgatt ctgaattgaa agcgcgcata tgggattcat   1020
tccttacggg gaaactcgag                                                1040
```

<210> SEQ ID NO 20
<211> LENGTH: 1187
<212> TYPE: DNA
<213> ORGANISM: Kluyveromyces marxianus

<400> SEQUENCE: 20

```
gaattcaggc aaagagagct gttgcacaga agcttttag gaaacttaaa ttgtcaagca      60
gacacaaatg ttacatttt tgtgttggat gcaacaacat ggttgagaca ttttgcgcat    120
atctataagc ttgccaccag taatgttttg aaatttgcca tttgtttaac aactttccag    180
gagttgagat ttcttcgtaa atcgaaggat gaaagcgtat tagaggccgc cactagagca    240
gtcatagcag tgagacaatt atactatgaa cgaaaccttc ttgctttgag atttacgggt    300
aacgttgctg acacttgga ggaacaccta gagatcgaag aacaaatgac atggaaatca     360
catgtggatg agtttgtcat agatgcaatt gcaaaagcac aagaaaagtt caacgtttta    420
aacaacgatg caatgcagaa cggaaaagac tgtatccctg tatctagcga tacccaagat    480
cccaagaagt ttaatttcat cagtttagtt actgacgact tcaatatgag aaataaagct    540
cagcaattgg ggattcgtac tttcagtact agatttgtat tcgccgtgtg cagggaactt    600
ggtagagaag caggtgtatg tactaattaa atctattcat atatcatatc ttaacgaaca    660
gacgtttgtt tattttatac atttttaaac ctctaatttg actaattaat tctacaacta    720
ttttattttt ttttaactca atttccagtt taaacaccaa aatacgtttc catataattg    780
aaaaaggaag tcatggttac attgaacgta actggcgttg gaggagcaaa gaccttgcaa    840
gataattgta ctaaattttg tatgatccgt tttcaatagc gttagtttat catttaaatt    900
acaattttgc tttatcttga cacgcaacca acatttatct gaactagtct ctctcataat    960
```

-continued

| | | |
|---|---|---|
| tcgtattttg gttgaggata gacaaaggct ggacttgacc gcggcggaag agttctgact | 1020 |
| tgatgcatca aaacccatta acaaattggt agccattgga gctgtgtggg ttttttttcct | 1080 |
| ggtaatacat ctagctttgc ttgcaacctt cgactttttct attagtgaat ttatcgatcc | 1140 |
| tttgccattg ccgccatcac gagaactttt attataggat tctcgag | 1187 |

<210> SEQ ID NO 21
<211> LENGTH: 1350
<212> TYPE: DNA
<213> ORGANISM: Kluyveromyces marxianus

<400> SEQUENCE: 21

| | |
|---|---|
| gaattcaata aggttttttt tggttttatg gaatggaatt tgagtgtaca tgtgttgtta | 60 |
| atggaatgtt gtaaacaagt gattattata aggcataatg ccaggaatct ttccataatt | 120 |
| tggaattgaa agtcacttta ggttcactat ataatgaaaa gaacacgata ataaaaactc | 180 |
| cgggatccgc taatatattt aatgatacac aggcatacat acatacatac atacaaacaa | 240 |
| aaacacacat ataaatattt ctcgttaagt gttcagatag gaggttcact ttctagctcc | 300 |
| tttaatctca tctgttctaa ttcttgtttg tcatcggcaa tagtaggcag agcaaagttg | 360 |
| ttaaagttgc tgctgtaaga gggtactgga tccgtcgggt agctcatagc gatatcactt | 420 |
| tccgaaagtg taacttctgg caacgtagac atgttctgtt gtaggaggta tccataaacc | 480 |
| tggtcaatgg gtgaacttgg ttcttccaat gaagtatttg ccgcattgtc gttcgtggtt | 540 |
| acatgtccat tatcctgggc gaccggaaca ccttctgcta caggtgactc ctgctgctgc | 600 |
| tgctgttgct gtgggatttc tctatgcgtc ccaagcacga tttcgataga cataccagtg | 660 |
| acatttctga gacgtttcaa acgatcaacg ttaatcaaat cttgaaagaa agtgacggac | 720 |
| tcatcttctc cagcggagtt gtgatctgaa gcaatcagtt ttggaatgaa cgagagtttt | 780 |
| tccgactgtg ttgggatatc gcttgtgcgt tgaccaccca ccaatctgtt tgattctgta | 840 |
| taaacctgat tcttcttgga caagtttgcc aagacttcaa cgtaatattg gaaagtgaaa | 900 |
| aacttgtttt tgacgtccga ggttgggaaa gtgtctaagg ggaccttttag ctttagcatt | 960 |
| accgatgcat catgggtatc tgggtctgta tatagtggtg ccacgctttg gcatatgtct | 1020 |
| tttctaaaag tctctgtttg ctctaggttt gcagaattag caactctgca aatccttacc | 1080 |
| aaagtagcga tcaagcctgc tggatgcgaa taatgtttat aatgcgagac tttgactttg | 1140 |
| acttggatat cttcccctac agtgtatccg agagacggga tttctacgga aatcttgact | 1200 |
| gttttgttgt tgttgttggt gttattatta ttattattat tgttgttgtt actggtgctc | 1260 |
| gcgctgctat tgttattgtt attgttggta ctattattat tattattgct attattttct | 1320 |
| gcgggacaag agtttcctga gttactcgag | 1350 |

<210> SEQ ID NO 22
<211> LENGTH: 1175
<212> TYPE: DNA
<213> ORGANISM: Kluyveromyces marxianus
<220> FEATURE:
<221> NAME/KEY: misc_feature
<222> LOCATION: (850)..(850)
<223> OTHER INFORMATION: "n" indicates unknown

<400> SEQUENCE: 22

| | |
|---|---|
| gaattcaaat ggtatatgtt taatgacttc ttggttgaag agattgagga agaagaagcc | 60 |
| ctccgtatct catactggtg gaagacacct gaaattgtcg tttattctga tgcagaagag | 120 |
| attagaaagc cttttgttcc agtttcagaa tacagtatag acgataatat attatatcgt | 180 |

-continued

```
gattacttca gtgaaggtat aaggaaagat gtcgttaggc aatacacatt acttactaga      240
gaggagccac ctggacctgg gaccttagtg gccctcgatg cagagtttgt gtccttgact      300
gaacctcgat tagaaattaa ttgtaaaggt atgaagactc tattaaaacc tgcaaagaaa      360
tctttagcac gtgtgtcact tttacgtgga gagggagaac ttgaaggtgt accttttatc      420
gatgattata ttataagcga gtgtcatatt gaagattatc taactcagtt cagtggaatt      480
gaaccgggtg atttagatcc taagttgagt aaaaagagct tggtaaagag acaagtcttt      540
tatagaaaga tctggctact ccttcaatta ggctgtgttt tgttgggca tggtttaacc       600 aatgatttcc gccagattaa tattcatgtt cctgcttctc aaatcagaga cacatctctc      660
tattatttga agggtaagag gtacttgtcg ttacgttatt tggcatatgc agtattgcat      720
aaacaagtcc aaactgggaa ccacgattcc attgaagatg cacacacagc cttactgttg      780
tacagaaaat acttgcaact gaaggaagaa ggtgtcttcg aaatgtacct tgaaaatatt      840
tatgatgaan gccggaaaat gggatttaga gttcctgaac agtatcctat gtagaattat      900
atatcatcga ttataatacg tttagtagta gaggtttgaa accgtttaat tgattcgtta      960
aaaacaacat gttgttctag ttttagatag tgttatcttt ttcgcttcaa aagttacttt     1020
ggattctaat ataagaaaaa aaataaaaac aaaccaaatc aaatgagagt tgatgaaata     1080
aacaaagata taatacgctt accactaccg aatataaata tcaagaat gctgctgacc       1140 caacacatac tccattcttc tattaacagc tcgag                                1175
```

<210> SEQ ID NO 23
<211> LENGTH: 1184
<212> TYPE: DNA
<213> ORGANISM: Kluyveromyces marxianus
<400> SEQUENCE: 23

```
gaattcaatc tactcacgag gttagtgctg gttgtgtcaa tttgattaaa aaaatactta       60
acagatcagt ggccaaaaga ccaactataa atgaaatagt ggaagatcca tggctcgcat      120
tataaaattc gaccaattaa atttttttaa aataaaaacg ctataatacg tgagtattgt      180
gcatgtcgat atacatctgc ttttttgaca atcctaagaa ttataatccg ccttaataat      240 ttaattaccct catatataat atataattgc catatatttt ctacttttaa ttctttaata    300
ttatttttca tttcaaaaag tgtgaaataa aaattaaaat gtcataacaa tttattaacg     360
acaaaataag agaataagaa aaagaatac aagccaaatg atataattta tttatattat      420
tcattataga cttcataatc ttcagagttt aaagctacag tatactctga ataattcttt     480
ttcacaaaga ataccagta gacagcacca accgccataa ctgctattcc actaactggg      540
aaaacccaat atgcatagcc gtcatttttcc acacttccat ttggcggtac gaatggaacg    600
acagccaaga aaagattaga gacaataaat attcccgtca atacatacca acttgtccat     660
ggtgtcggga tcattccaa attgtcatta tttgtccaat gcatatatac caacccaact       720
ccgataatta gattgaacca accacttgga tacgcgtaaa gatcaataat taattgataa     780
acgttaccat ttggtggaat tatgaggacc aaaatagtga caaagcagtg taaaaataga    840
gcgtagttta atttactgaa aatatgcgta aaggggaaaa ttccttcttt agcaagttct    900
tggtttactc tggcatttga gaactaacg gccataacgt taccataatt tgaaagtgtt      960
atgcagaagg gtaaaagcg tgaaacaatc tgtgccgcca aagattttga gtatttctca     1020 aaaatttct caaagaaaac accacttatg aggataccg tatttgatat ttcatctttg      1080
```

```
gggattacaa tgtagtacga gatcactatt gcaatatata ggaaagttgt aagaccaacc   1140
gatactggtg ctgcaatcat tagagttttta tgaggatcct cgag                  1184
```

<210> SEQ ID NO 24
<211> LENGTH: 568
<212> TYPE: DNA
<213> ORGANISM: Kluyveromyces marxianus

<400> SEQUENCE: 24

```
gaattcctca gaattagaag tacgtagtag aaggtttctt gtcgctatac tcgttttagt    60
aagttttttg tatgtgtatg tattgtactt aagcgtaggg caggacccct caggacgaca   120
atattgtcaa aaataaata caacaaaatg agaaagagaa aaatatttaa agatttaaga    180
aggaaaaaga gaattgggaa aggaaagtgg aaattgggtt ctcggctgtt tttcgatata   240
ctatactcgc atgagggaac aagtttcaga cgatggataa cacgtgagat catcatttgt   300
gtatccaccg gtgcatctag cggcttttcta tttggctttg aagtcggatc tgactgacaa   360
aaaaatagtg ctagaaagct actacaatca gttataagat ttagacgata atgagatgtg   420
caaaacccta gtgacaccag tcttcggtgc ttttcacatc aaccaaccgt catcactaaa   480
ttcaacccac taagtagttg caaaagattt tagatggtga atgaaagtg agaatttaga    540 taggaaagat agagaatcca tgctcgag                                      568
```

<210> SEQ ID NO 25
<211> LENGTH: 795
<212> TYPE: DNA
<213> ORGANISM: Kluyveromyces marxianus

<400> SEQUENCE: 25

```
gaattcagat atgacaatga gaggtacagt ttttttggatg gcgccagaga tggtggatac    60
tgcccatgga tacagtgcta aagtagatat atggtctctc ggatgtgttg tattggaaat   120
gtatgctggt aagagaccgt ggtcaaattt cgaagttgtt gctgctatgt tccagatagg   180
gaaatctaag actgcgcctc ctataacctga cgatacaaaa gacttaatat cagcaagtgg   240
taaaaacttt ttagacatgt gttttcgaaat aaacccggag aaaagaccta ccgctgattt   300
cttagtgagt cacccccttct gtaaaacaga tccgtcattc gattttttcta aaactaaact   360 agcccaattc atcaggtcaa atgataaact aaacaacagt aagttacgta tcagctcaca   420
agagttatga agcttggatt tattgagtgt cttgttatat acatacgtat tatgctctaa   480
aacttctttt aatatttatg aataaaagta acttttttagt ttcaaatact aaaaaatatt   540
aattacaaag taacaatata accaattatt acaaaaaaat gccagatact acacaaggaa   600
ttacgtttat taagtatgat catgggattt catttcccca atttcgacat cttctaaaag   660
atcatctaaa atttcattaa gcatgtcaga aagacggtat gtcaaatata atgattgctt   720
gaaaggatat cggagaggag attcctcaga aatccaaaag agctttgatt gtgactggtt   780 taaacgttttc tcgag                                                   795
```